US011883217B2

(12) United States Patent
Johnson et al.

(10) Patent No.: US 11,883,217 B2
(45) Date of Patent: Jan. 30, 2024

(54) PORTABLE MEDICAL IMAGING SYSTEM AND METHOD

(71) Applicant: GLOBUS MEDICAL, INC., Audubon, PA (US)

(72) Inventors: Norbert Johnson, North Andover, MA (US); Robert Stevens, North Chelmsford, MA (US); Hisham Salem, Newton, MA (US); Yuan Cheng, Andover, MA (US); David Cleary, Somerville, MA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/180,746

(22) Filed: Nov. 5, 2018

(65) Prior Publication Data

US 2019/0150865 A1    May 23, 2019

Related U.S. Application Data

(63) Continuation-in-part of application No. 15/180,126, filed on Jun. 13, 2016, now Pat. No. 10,842,453, (Continued)

(51) Int. Cl.
*A61B 6/00* (2006.01)
*A61B 6/03* (2006.01)

(52) U.S. Cl.
CPC .......... *A61B 6/4405* (2013.01); *A61B 6/4441* (2013.01); *A61B 6/4447* (2013.01);
(Continued)

(58) Field of Classification Search
CPC ... A61B 6/4405; A61B 6/4441; A61B 6/4447; A61B 6/485; A61B 6/547; A61B 6/032; A61B 6/035; A61B 6/4085; A61B 6/56
See application file for complete search history.

(56) References Cited

U.S. PATENT DOCUMENTS

| 4,150,293 A | 4/1979 | Franke |
| 5,020,933 A | 6/1991 | Salvestro et al. |

(Continued)

FOREIGN PATENT DOCUMENTS

| AU | 2015234609 A1 | 10/2016 |
| CN | 1536975 A | 10/2004 |

(Continued)

OTHER PUBLICATIONS

US 8,231,638 B2, 07/2012, Swarup et al. (withdrawn)
(Continued)

*Primary Examiner* — David J Makiya
*Assistant Examiner* — Soorena Kefayati

(57) ABSTRACT

A portable medical imaging system and method, of which the system includes a movable station having a movable C-arm, an imaging signal transmitter attached to the movable C-arm, and an imaging sensor positioned generally opposite to the imaging signal transmitter and attached to the movable c-arm. The imaging sensor is configured to rotate relative to a point approximately on a center axis of the movable C-arm independently of the imaging signal transmitter, so as to change an angle of incidence for a signal transmitted from the imaging signal transmitter to the imaging sensor, and provide a field-of-view that is larger than the field-of-view of the imaging sensor at a single position.

17 Claims, 18 Drawing Sheets

Related U.S. Application Data which is a continuation-in-part of application No. 15/014,083, filed on Feb. 3, 2016, now Pat. No. 10,448,910.

(52) U.S. Cl.
CPC .............. *A61B 6/547* (2013.01); *A61B 6/032* (2013.01); *A61B 6/035* (2013.01); *A61B 6/4085* (2013.01); *A61B 6/485* (2013.01); *A61B 6/56* (2013.01)

(56) References Cited

U.S. PATENT DOCUMENTS

| | | | |
|---|---|---|---|
| 5,246,010 A | 9/1993 | Gazzara et al. | |
| 5,354,314 A | 10/1994 | Hardy et al. | |
| 5,397,323 A | 3/1995 | Taylor et al. | |
| 5,410,584 A * | 4/1995 | Schaefer | A61B 6/4441 |
| | | | 378/196 |
| 5,598,453 A | 1/1997 | Baba et al. | |
| 5,772,594 A | 6/1998 | Barrick | |
| 5,791,908 A | 8/1998 | Gillio | |
| 5,820,559 A | 10/1998 | Ng et al. | |
| 5,825,982 A | 10/1998 | Wright et al. | |
| 5,887,121 A | 3/1999 | Funda et al. | |
| 5,911,449 A | 6/1999 | Daniele et al. | |
| 5,951,475 A | 9/1999 | Gueziec et al. | |
| 5,987,960 A | 11/1999 | Messner et al. | |
| 6,012,216 A | 1/2000 | Esteves et al. | |
| 6,031,888 A | 2/2000 | Ivan et al. | |
| 6,033,415 A | 3/2000 | Mittelstadt et al. | |
| 6,080,181 A | 6/2000 | Jensen et al. | |
| 6,106,511 A | 8/2000 | Jensen | |
| 6,113,264 A * | 9/2000 | Watanabe | A61B 6/466 |
| | | | 378/197 |
| 6,122,541 A | 9/2000 | Cosman et al. | |
| 6,144,875 A | 11/2000 | Schweikard et al. | |
| 6,157,853 A | 12/2000 | Blume et al. | |
| 6,167,145 A | 12/2000 | Foley et al. | |
| 6,167,292 A | 12/2000 | Badano et al. | |
| 6,201,984 B1 | 3/2001 | Funda et al. | |
| 6,203,196 B1 * | 3/2001 | Meyer | A61B 6/4441 |
| | | | 378/197 |
| 6,205,411 B1 | 3/2001 | DiGioia, III et al. | |
| 6,212,419 B1 | 4/2001 | Blume et al. | |
| 6,231,565 B1 | 5/2001 | Tovey et al. | |
| 6,236,875 B1 | 5/2001 | Bucholz et al. | |
| 6,246,900 B1 | 6/2001 | Cosman et al. | |
| 6,301,495 B1 | 10/2001 | Gueziec et al. | |
| 6,306,126 B1 | 10/2001 | Montezuma | |
| 6,312,435 B1 | 11/2001 | Wallace et al. | |
| 6,314,311 B1 | 11/2001 | Williams et al. | |
| 6,320,929 B1 | 11/2001 | Von Der Haar | |
| 6,322,567 B1 | 11/2001 | Mittelstadt et al. | |
| 6,325,808 B1 | 12/2001 | Bernard et al. | |
| 6,340,363 B1 | 1/2002 | Bolger et al. | |
| 6,377,011 B1 | 4/2002 | Ben-Ur | |
| 6,379,302 B1 | 4/2002 | Kessman et al. | |
| 6,402,762 B2 | 6/2002 | Hunter et al. | |
| 6,424,885 B1 | 7/2002 | Niemeyer et al. | |
| 6,447,503 B1 | 9/2002 | Wynne et al. | |
| 6,451,027 B1 | 9/2002 | Cooper et al. | |
| 6,477,400 B1 | 11/2002 | Barrick | |
| 6,484,049 B1 | 11/2002 | Seeley et al. | |
| 6,487,267 B1 | 11/2002 | Wolter | |
| 6,490,467 B1 | 12/2002 | Bucholz et al. | |
| 6,490,475 B1 | 12/2002 | Seeley et al. | |
| 6,499,488 B1 | 12/2002 | Hunter et al. | |
| 6,501,981 B1 | 12/2002 | Schweikard et al. | |
| 6,507,751 B2 | 1/2003 | Blume et al. | |
| 6,535,756 B1 | 3/2003 | Simon et al. | |
| 6,560,354 B1 | 5/2003 | Maurer, Jr. et al. | |
| 6,565,554 B1 | 5/2003 | Niemeyer | |
| 6,587,750 B2 | 7/2003 | Gerbi et al. | |
| 6,614,453 B1 | 9/2003 | Suri et al. | |
| 6,614,871 B1 | 9/2003 | Kobiki et al. | |
| 6,619,840 B2 * | 9/2003 | Rasche | A61B 6/032 |
| | | | 378/197 |
| 6,636,757 B1 | 10/2003 | Jascob et al. | |
| 6,645,196 B1 | 11/2003 | Nixon et al. | |
| 6,666,579 B2 | 12/2003 | Jensen | |
| 6,669,635 B2 | 12/2003 | Kessman et al. | |
| 6,701,173 B2 | 3/2004 | Nowinski et al. | |
| 6,757,068 B2 | 6/2004 | Foxlin | |
| 6,782,287 B2 | 8/2004 | Grzeszczuk et al. | |
| 6,783,524 B2 | 8/2004 | Anderson et al. | |
| 6,786,896 B1 | 9/2004 | Madhani et al. | |
| 6,788,018 B1 | 9/2004 | Blumenkranz | |
| 6,804,581 B2 | 10/2004 | Wang et al. | |
| 6,823,207 B1 | 11/2004 | Jensen et al. | |
| 6,827,351 B2 | 12/2004 | Graziani et al. | |
| 6,837,892 B2 | 1/2005 | Shoham | |
| 6,839,612 B2 | 1/2005 | Sanchez et al. | |
| 6,856,826 B2 | 2/2005 | Seeley et al. | |
| 6,856,827 B2 | 2/2005 | Seeley et al. | |
| 6,879,880 B2 | 4/2005 | Nowlin et al. | |
| 6,892,090 B2 | 5/2005 | Verard et al. | |
| 6,920,347 B2 | 7/2005 | Simon et al. | |
| 6,922,632 B2 | 7/2005 | Foxlin | |
| 6,968,224 B2 | 11/2005 | Kessman et al. | |
| 6,978,166 B2 | 12/2005 | Foley et al. | |
| 6,988,009 B2 | 1/2006 | Grimm et al. | |
| 6,991,627 B2 | 1/2006 | Madhani et al. | |
| 6,996,487 B2 | 2/2006 | Jutras et al. | |
| 6,999,852 B2 | 2/2006 | Green | |
| 7,007,699 B2 | 3/2006 | Martinelli et al. | |
| 7,016,457 B1 | 3/2006 | Senzig et al. | |
| 7,043,961 B2 | 5/2006 | Pandey et al. | |
| 7,062,006 B1 | 6/2006 | Pelc et al. | |
| 7,063,705 B2 | 6/2006 | Young et al. | |
| 7,072,707 B2 | 7/2006 | Galloway, Jr. et al. | |
| 7,083,615 B2 | 8/2006 | Peterson et al. | |
| 7,097,640 B2 | 8/2006 | Wang et al. | |
| 7,099,428 B2 | 8/2006 | Clinthorne et al. | |
| 7,108,421 B2 * | 9/2006 | Gregerson | A61B 6/4405 |
| | | | 378/146 |
| 7,130,676 B2 | 10/2006 | Barrick | |
| 7,139,418 B2 | 11/2006 | Abovitz et al. | |
| 7,139,601 B2 | 11/2006 | Bucholz et al. | |
| 7,155,316 B2 | 12/2006 | Sutherland et al. | |
| 7,164,968 B2 | 1/2007 | Treat et al. | |
| 7,167,738 B2 | 1/2007 | Schweikard et al. | |
| 7,169,141 B2 | 1/2007 | Brock et al. | |
| 7,172,627 B2 | 2/2007 | Fiere et al. | |
| 7,182,083 B2 | 2/2007 | Yanof et al. | |
| 7,194,120 B2 | 3/2007 | Wicker et al. | |
| 7,197,107 B2 | 3/2007 | Arai et al. | |
| 7,207,995 B1 | 4/2007 | Vandewalle | |
| 7,231,014 B2 | 6/2007 | Levy | |
| 7,231,063 B2 | 6/2007 | Naimark et al. | |
| 7,239,940 B2 | 7/2007 | Wang et al. | |
| 7,248,914 B2 | 7/2007 | Tastings et al. | |
| 7,301,648 B2 | 11/2007 | Foxlin | |
| 7,302,288 B1 | 11/2007 | Schellenberg | |
| 7,313,430 B2 | 12/2007 | Urquhart et al. | |
| 7,318,805 B2 | 1/2008 | Schweikard et al. | |
| 7,318,827 B2 | 1/2008 | Leitner et al. | |
| 7,319,897 B2 | 1/2008 | Leitner et al. | |
| 7,324,623 B2 | 1/2008 | Heuscher et al. | |
| 7,327,865 B2 | 2/2008 | Fu et al. | |
| 7,331,967 B2 | 2/2008 | Lee et al. | |
| 7,333,642 B2 | 2/2008 | Green | |
| 7,339,341 B2 | 3/2008 | Oleynikov et al. | |
| 7,366,562 B2 | 4/2008 | Dukesherer et al. | |
| 7,379,790 B2 | 5/2008 | Toth et al. | |
| 7,386,365 B2 | 6/2008 | Nixon | |
| 7,422,592 B2 | 9/2008 | Morley et al. | |
| 7,435,216 B2 | 10/2008 | Kwon et al. | |
| 7,440,793 B2 | 10/2008 | Chauhan et al. | |
| 7,460,637 B2 | 12/2008 | Clinthorne et al. | |
| 7,466,303 B2 | 12/2008 | Yi et al. | |
| 7,493,153 B2 | 2/2009 | Ahmed et al. | |
| 7,505,617 B2 | 3/2009 | Fu et al. | |
| 7,533,892 B2 | 5/2009 | Schena et al. | |

(56) References Cited

U.S. PATENT DOCUMENTS

| | | |
|---|---|---|
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 * | 5/2010 | Heigl .................. A61B 6/032 378/20 |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 * | 9/2010 | Bergfjord ............ A61B 6/4035 378/65 |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,313,430 B1 | 11/2012 | Pimenta |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |

(56) References Cited

U.S. PATENT DOCUMENTS

| | | |
|---|---|---|
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 * | 6/2013 | Vesel .......... A61B 6/4441 378/210 |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 * | 3/2014 | Gregerson .......... A61B 6/4085 378/197 |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 * | 4/2015 | Sowards-Emmerd ................ G06T 11/006 378/11 |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |

(56) References Cited

U.S. PATENT DOCUMENTS

| | | |
|---|---|---|
| 9,414,859 B2 | 8/2016 | Ballard et al. |
| 9,420,975 B2 | 8/2016 | Gutfleisch et al. |
| 9,463,073 B2 | 10/2016 | Gill et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 10,575,906 B2 | 3/2020 | Wu |
| 2001/0036302 A1 | 11/2001 | Miller |
| 2002/0035321 A1 | 3/2002 | Bucholz et al. |
| 2003/0125622 A1 | 7/2003 | Schweikard et al. |
| 2003/0152195 A1* | 8/2003 | Hebecker ............... A61B 6/547 378/162 |
| 2003/0161442 A1 | 8/2003 | Zeiss |
| 2004/0013225 A1* | 1/2004 | Gregerson ............ A61B 6/4405 378/19 |
| 2004/0019263 A1 | 1/2004 | Jutras et al. |
| 2004/0024311 A1 | 2/2004 | Quaid |
| 2004/0034302 A1 | 2/2004 | Abovitz et al. |
| 2004/0068172 A1 | 4/2004 | Nowinski et al. |
| 2004/0076259 A1 | 4/2004 | Jensen et al. |
| 2004/0097952 A1 | 5/2004 | Sarin et al. |
| 2004/0153191 A1 | 8/2004 | Grimm et al. |
| 2004/0157188 A1 | 8/2004 | Luth et al. |
| 2004/0215071 A1 | 10/2004 | Frank et al. |
| 2005/0085714 A1 | 4/2005 | Foley et al. |
| 2005/0096502 A1 | 5/2005 | Khalili |
| 2005/0107679 A1 | 5/2005 | Geiger et al. |
| 2005/0119639 A1 | 6/2005 | McCombs et al. |
| 2005/0143651 A1 | 6/2005 | Verard et al. |
| 2005/0149045 A1 | 7/2005 | Elliott |
| 2005/0171558 A1 | 8/2005 | Abovitz et al. |
| 2006/0036264 A1 | 2/2006 | Selover et al. |
| 2006/0100610 A1 | 5/2006 | Wallace et al. |
| 2006/0142657 A1 | 6/2006 | Quaid et al. |
| 2006/0153340 A1* | 7/2006 | Engstrom ............ A61B 6/4441 378/197 |
| 2006/0173329 A1 | 8/2006 | Marquart et al. |
| 2006/0178559 A1 | 8/2006 | Kumar et al. |
| 2006/0184396 A1 | 8/2006 | Dennis et al. |
| 2006/0210015 A1 | 9/2006 | Pele et al. |
| 2006/0241416 A1 | 10/2006 | Marquart et al. |
| 2006/0264963 A1 | 11/2006 | Reed et al. |
| 2006/0274888 A1* | 12/2006 | Bernhardt .......... G05B 19/4061 378/117 |
| 2006/0291612 A1 | 12/2006 | Nishide et al. |
| 2007/0001879 A1 | 1/2007 | Kaftan et al. |
| 2007/0015987 A1 | 1/2007 | Benlloch Baviera et al. |
| 2007/0016009 A1 | 1/2007 | Lakin et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0078475 A1 | 4/2007 | Bodduluri et al. |
| 2007/0086566 A1* | 4/2007 | Gregerson ............ A61B 6/4405 378/19 |
| 2007/0121790 A1* | 5/2007 | Grady ................. A61B 6/4441 378/198 |
| 2007/0122020 A1* | 5/2007 | Claus ..................... A61B 6/583 382/131 |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0238985 A1 | 10/2007 | Smith et al. |
| 2008/0004523 A1 | 1/2008 | Jensen |
| 2008/0010706 A1 | 1/2008 | Moses et al. |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0119725 A1 | 5/2008 | Lloyd |
| 2008/0144906 A1 | 6/2008 | Allred et al. |
| 2008/0154389 A1 | 6/2008 | Smith et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0188934 A1 | 8/2008 | Moser et al. |
| 2008/0214922 A1 | 9/2008 | Hartmann et al. |
| 2008/0228068 A1 | 9/2008 | Viswanathan et al. |
| 2008/0228195 A1 | 9/2008 | von Jako et al. |
| 2008/0228196 A1 | 9/2008 | Wang et al. |
| 2008/0235052 A1 | 9/2008 | Node-Langlois et al. |
| 2008/0258929 A1* | 10/2008 | Maschke ............... A61B 6/547 340/686.1 |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0099445 A1 | 4/2009 | Burger |
| 2009/0180586 A1* | 7/2009 | Fehre .................... A61B 6/4429 378/209 |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0234217 A1 | 9/2009 | Mire et al. |
| 2009/0240141 A1 | 9/2009 | Neubauer et al. |
| 2009/0254326 A1 | 10/2009 | Isaacs |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2009/0306480 A1 | 12/2009 | Protopsaltis |
| 2009/0306499 A1 | 12/2009 | Van Vorhis et al. |
| 2010/0022874 A1 | 1/2010 | Wang et al. |
| 2010/0039506 A1 | 2/2010 | Sarvestani et al. |
| 2010/0076305 A1 | 3/2010 | Maier-Hein et al. |
| 2010/0114288 A1 | 5/2010 | Haller et al. |
| 2010/0125286 A1 | 5/2010 | Wang et al. |
| 2010/0130986 A1 | 5/2010 | Mailloux et al. |
| 2010/0172472 A1* | 7/2010 | Ermes .................... A61B 6/5241 250/336.1 |
| 2010/0174410 A1 | 7/2010 | Greer et al. |
| 2010/0183118 A1* | 7/2010 | Star-Lack ............ A61N 5/1049 378/23 |
| 2010/0228117 A1 | 9/2010 | Hartmann |
| 2010/0228265 A1 | 9/2010 | Prisco |
| 2010/0228340 A1 | 9/2010 | Erbel et al. |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0019884 A1 | 1/2011 | Blau |
| 2011/0020084 A1 | 1/2011 | Brett et al. |
| 2011/0022229 A1 | 1/2011 | Jang et al. |
| 2011/0040305 A1 | 2/2011 | Gomez et al. |
| 2011/0071347 A1 | 3/2011 | Rogers et al. |
| 2011/0077504 A1 | 3/2011 | Fischer et al. |
| 2011/0082468 A1 | 4/2011 | Hagag et al. |
| 2011/0098553 A1 | 4/2011 | Robbins et al. |
| 2011/0137152 A1 | 6/2011 | Li |
| 2011/0184245 A1 | 7/2011 | Xia et al. |
| 2011/0190588 A1 | 8/2011 | McKay |
| 2011/0213379 A1 | 9/2011 | Blau et al. |
| 2011/0213384 A1 | 9/2011 | Jeong |

(56) References Cited

U.S. PATENT DOCUMENTS

| | | |
|---|---|---|
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Arkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0257653 A1 | 10/2011 | Hughes et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306873 A1 | 12/2011 | Shenai et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0051647 A1 | 2/2013 | Miao et al. |
| 2013/0060146 A1 | 3/2013 | Yang et al. |
| 2013/0060337 A1 | 3/2013 | Petersheim et al. |
| 2013/0064427 A1 | 3/2013 | Picard et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0121459 A1* | 5/2013 | Meyer .................. A61B 6/4441 378/9 |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0165948 A1 | 6/2013 | Popovic |
| 2013/0178867 A1 | 7/2013 | Farritor et al. |
| 2013/0178868 A1 | 7/2013 | Roh |
| 2013/0178870 A1 | 7/2013 | Schena |
| 2013/0184873 A1 | 7/2013 | Namiki |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0268007 A1 | 10/2013 | Rezach et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0279784 A1 | 10/2013 | Gill |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1 | 12/2013 | Crawford et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0067343 A1 | 3/2014 | Yamagata |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088410 A1 | 3/2014 | Wu |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0200587 A1 | 7/2014 | Pompee et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276943 A1 | 9/2014 | Bowling et al. |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316420 A1 | 10/2014 | Ballard et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0336669 A1 | 11/2014 | Park |
| 2014/0343416 A1 | 11/2014 | Panescu et al. |
| 2014/0357989 A1 | 12/2014 | Hendriks et al. |
| 2014/0364720 A1 | 12/2014 | Darrow et al. |
| 2014/0371577 A1 | 12/2014 | Maillet et al. |

(56) References Cited

U.S. PATENT DOCUMENTS

| | | | |
|---|---|---|---|
| 2015/0032164 A1* | 1/2015 | Crawford | A61B 17/7074 606/279 |
| 2015/0039034 A1 | 2/2015 | Frankel et al. | |
| 2015/0049174 A1 | 2/2015 | Lee et al. | |
| 2015/0085970 A1 | 3/2015 | Bouhnik et al. | |
| 2015/0100066 A1 | 4/2015 | Kostrzewski et al. | |
| 2015/0100067 A1 | 4/2015 | Cavanagh et al. | |
| 2015/0146847 A1 | 5/2015 | Liu | |
| 2015/0150524 A1 | 6/2015 | Yorkston et al. | |
| 2015/0157416 A1 | 6/2015 | Andersson | |
| 2015/0157468 A1 | 6/2015 | Wakayama et al. | |
| 2015/0173810 A1 | 6/2015 | Biedermann et al. | |
| 2015/0196261 A1 | 7/2015 | Funk | |
| 2015/0196365 A1 | 7/2015 | Kostrzewski et al. | |
| 2015/0213633 A1* | 7/2015 | Chang | A61B 6/032 382/284 |
| 2015/0320370 A1* | 11/2015 | Bouvier | A61B 6/4441 378/189 |
| 2015/0335480 A1 | 11/2015 | Alvarez et al. | |
| 2015/0342647 A1 | 12/2015 | Frankel et al. | |
| 2016/0005194 A1 | 1/2016 | Schretter et al. | |
| 2016/0030129 A1 | 2/2016 | Christian et al. | |
| 2016/0033284 A1 | 2/2016 | Sato | |
| 2016/0063707 A1 | 3/2016 | Masumoto | |
| 2016/0082596 A1* | 3/2016 | Barth | A61B 6/4405 901/1 |
| 2016/0166329 A1* | 6/2016 | Langan | A61B 6/4014 600/424 |
| 2016/0220320 A1 | 8/2016 | Crawford et al. | |
| 2016/0235480 A1 | 8/2016 | Scholl et al. | |
| 2016/0235492 A1 | 8/2016 | Morard et al. | |
| 2016/0235493 A1 | 8/2016 | LeBoeuf et al. | |
| 2016/0249990 A1 | 9/2016 | Glozman et al. | |
| 2016/0256225 A1 | 9/2016 | Crawford et al. | |
| 2016/0296266 A1 | 10/2016 | Chandanson et al. | |
| 2016/0302871 A1 | 10/2016 | Gregerson et al. | |
| 2016/0320322 A1 | 11/2016 | Suzuki | |
| 2016/0331335 A1 | 11/2016 | Gregerson et al. | |
| 2017/0000562 A1 | 1/2017 | Frank et al. | |
| 2017/0007327 A1 | 1/2017 | Haider et al. | |
| 2017/0020609 A1 | 1/2017 | Wentorf et al. | |
| 2017/0079727 A1 | 3/2017 | Crawford et al. | |
| 2017/0112552 A1 | 4/2017 | Sinnott et al. | |
| 2017/0135770 A1 | 5/2017 | Scholl et al. | |
| 2017/0143284 A1 | 5/2017 | Sehnert et al. | |
| 2017/0143426 A1 | 5/2017 | Isaacs et al. | |
| 2017/0156816 A1 | 6/2017 | Ibrahim | |
| 2017/0189126 A1 | 7/2017 | Weir | |
| 2017/0202629 A1 | 7/2017 | Maillet et al. | |
| 2017/0209222 A1 | 7/2017 | Gassner et al. | |
| 2017/0212723 A1 | 7/2017 | Atarot et al. | |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |
| 2017/0231710 A1 | 8/2017 | Scholl et al. | |
| 2017/0245946 A1 | 8/2017 | Tabandeh et al. | |
| 2017/0245951 A1 | 8/2017 | Crawford et al. | |
| 2017/0258426 A1 | 9/2017 | Risher-Kelly et al. | |
| 2017/0258526 A1 | 9/2017 | Lang | |
| 2017/0258532 A1 | 9/2017 | Shalayev et al. | |
| 2017/0258535 A1 | 9/2017 | Crawford et al. | |
| 2017/0265952 A1 | 9/2017 | Donhowe et al. | |
| 2017/0273748 A1 | 9/2017 | Hourtash et al. | |
| 2017/0296277 A1 | 10/2017 | Hourtash et al. | |
| 2017/0312032 A1 | 11/2017 | Amanatullah et al. | |
| 2017/0333137 A1 | 11/2017 | Roessler | |
| 2017/0348061 A1 | 12/2017 | Joshi et al. | |
| 2017/0360493 A1 | 12/2017 | Zucher et al. | |
| 2018/0008355 A1 | 1/2018 | Mozes et al. | |
| 2018/0042464 A1 | 2/2018 | Arai et al. | |
| 2018/0049825 A1 | 2/2018 | Kwon et al. | |
| 2018/0064496 A1 | 3/2018 | Hladio et al. | |
| 2018/0064497 A1 | 3/2018 | Hussain et al. | |
| 2018/0066794 A1 | 3/2018 | Okuda et al. | |
| 2018/0092699 A1 | 4/2018 | Finley | |
| 2018/0200016 A1 | 7/2018 | Chappuis | |
| 2018/0249981 A1 | 9/2018 | Johnson et al. | |
| 2018/0325608 A1 | 11/2018 | Kang et al. | |
| 2018/0325610 A1 | 11/2018 | Cameron et al. | |

FOREIGN PATENT DOCUMENTS

| | | |
|---|---|---|
| CN | 1714742 A | 1/2006 |
| CN | 102036615 A | 4/2011 |
| CN | 202027725 U | 11/2011 |
| CN | 102438551 A | 5/2012 |
| CN | 102596062 A | 7/2012 |
| CN | 102612350 A | 7/2012 |
| CN | 102933163 A | 2/2013 |
| CN | 103945764 A | 7/2014 |
| CN | 104334110 A | 2/2015 |
| CN | 104994805 A | 10/2015 |
| CN | 105101903 A | 11/2015 |
| CN | 105939687 A | 9/2016 |
| CN | 106163446 A | 11/2016 |
| CN | 106691600 A | 5/2017 |
| CN | 106999168 A | 8/2017 |
| CN | 106999245 A | 8/2017 |
| CN | 107088091 A | 8/2017 |
| CN | 107405170 A | 11/2017 |
| CN | 107545585 A | 1/2018 |
| CN | 108601569 A | 9/2018 |
| CN | 108652743 B | 10/2018 |
| CN | 209153975 U | 7/2019 |
| CN | 107847275 B | 10/2020 |
| DE | 102014221469 A1 | 4/2016 |
| DE | 102012215001 B4 | 12/2021 |
| EP | 1224918 A2 | 7/2002 |
| EP | 1346687 A1 | 9/2003 |
| EP | 2468207 A1 | 6/2012 |
| EP | 2471483 A1 | 7/2012 |
| EP | 2471617 A1 | 7/2012 |
| EP | 3181085 A1 | 6/2017 |
| EP | 3391848 A2 | 10/2018 |
| EP | 3517069 A1 | 7/2019 |
| JP | 3-118053 A | 5/1991 |
| JP | 11-313837 A | 11/1999 |
| JP | 2001135734 A | 5/2001 |
| JP | 2002253574 A | 9/2002 |
| JP | 2004518475 A | 6/2004 |
| JP | 2005-533579 A | 11/2005 |
| JP | 2007-044488 A | 2/2007 |
| JP | 2007-531543 A | 11/2007 |
| JP | 2007534351 A | 11/2007 |
| JP | 2007537835 A | 12/2007 |
| JP | 2008-507361 A | 3/2008 |
| JP | 2008507361 A | 3/2008 |
| JP | 2008188417 A | 8/2008 |
| JP | 2008-538184 A | 10/2008 |
| JP | 2009537229 A | 10/2009 |
| JP | 2011-120782 A | 6/2011 |
| JP | 2011-517594 A | 6/2011 |
| JP | 2012075507 A | 4/2012 |
| JP | 2013075195 A | 4/2013 |
| JP | 2013-541365 A | 11/2013 |
| JP | 2014036700 A | 2/2014 |
| JP | 2014-48228 A | 3/2014 |
| JP | 2014097220 A | 5/2014 |
| JP | 2015-504721 A | 2/2015 |
| JP | 201536161 A | 2/2015 |
| JP | 2015100677 A | 6/2015 |
| JP | 2015119968 A | 7/2015 |
| JP | 2015521084 A | 7/2015 |
| JP | 2015528713 A | 10/2015 |
| JP | 2015-534480 A | 12/2015 |
| JP | 2015534845 A | 12/2015 |
| JP | 2016-33474 A | 3/2016 |
| JP | 2016043211 A | 4/2016 |
| JP | 2016185225 A | 10/2016 |
| JP | 2016-193222 A | 11/2016 |
| JP | 2016193222 A | 11/2016 |
| JP | 2016539681 A | 12/2016 |
| JP | 2017087313 A | 5/2017 |

(56) References Cited

FOREIGN PATENT DOCUMENTS

| | | |
|---|---|---|
| JP | 2017-528255 A | 9/2017 |
| JP | 2017176848 A | 10/2017 |
| JP | 2017530842 A | 10/2017 |
| JP | 2017221660 A | 12/2017 |
| JP | 2017223657 A | 12/2017 |
| JP | 2018011938 A | 1/2018 |
| JP | 2018-027288 A | 2/2018 |
| JP | 2018516107 A | 6/2018 |
| JP | 2018-114283 A | 7/2018 |
| JP | 2018523516 A | 8/2018 |
| JP | 2018-202156 A | 12/2018 |
| JP | 2021-25802 A | 2/2021 |
| JP | 2021025802 A | 2/2021 |
| WO | 03007198 A2 | 1/2003 |
| WO | 2009092164 A1 | 7/2009 |
| WO | 2009126953 A2 | 10/2009 |
| WO | 2011128766 A2 | 10/2011 |
| WO | 2012050634 A1 | 4/2012 |
| WO | 2013114823 A1 | 8/2013 |
| WO | 2013118047 A1 | 8/2013 |
| WO | 2013192598 A1 | 12/2013 |
| WO | 2014010760 A1 | 1/2014 |
| WO | 2014062890 A1 | 4/2014 |
| WO | 2014139023 A1 | 9/2014 |
| WO | 2015052718 A1 | 4/2015 |
| WO | 2015061638 A1 | 4/2015 |
| WO | 2015079775 A1 | 6/2015 |
| WO | 2015142762 A1 | 9/2015 |
| WO | 201613049 A1 | 1/2016 |
| WO | 2016087539 A2 | 6/2016 |
| WO | 2016114834 A2 | 7/2016 |
| WO | 2016152255 A1 | 9/2016 |
| WO | 2016154557 A1 | 9/2016 |
| WO | 2016170372 A1 | 10/2016 |
| WO | 2017221257 A1 | 2/2017 |
| WO | 2017127202 A1 | 7/2017 |
| WO | 2017147596 A1 | 8/2017 |
| WO | 2017186799 A1 | 11/2017 |
| WO | 2017204832 A1 | 11/2017 |
| WO | 2017221257 A1 | 12/2017 |
| WO | 2018075784 A1 | 4/2018 |
| WO | 2018165767 A1 | 9/2018 |
| WO | 2018183461 A1 | 10/2018 |
| WO | 2019193775 A1 | 10/2019 |

OTHER PUBLICATIONS

*Nevro Corp.* v. *Boston Scientific Corp et al*, U.S. Dist. Court ND California, Complaint for Patent Infringement and Declaratory Judgement, Case No. 16-cv-6830, 10 pages.
State of the Art Search for Imaging Devices Used in Conjunction With Surgical Navigation Software for Registering Image Data, performed by Shane Davis of Optimized Intellectual Property Solutions, Nov. 5, 2014, 2 pages.
Search Report for: Automatic Planning of Surgical Screw Position During a Robot Assisted Surgical Procedure by John Johnson, dated Jan. 18, 2018, 2 pages.
Search Report for: Breathing Meter for Robotic Assisted Surgery by John Johnson, dated Jan. 22, 2018, 3 pages.
Search Report for: Instrument Verification Improvement by John Johnson, dated May 22, 2018, 2 pages.
Search Report for: Hammerhead Probe by John Johnson, dated Jul. 3, 2018, 2 pages.
Search Report for: Navigation of a Bent Rod by John Johnson, dated Jul. 6, 2018, 2 pages.
Search Report for: Large Field of View Cone Beam CT by John Johnson, dated Jul. 12, 2018, 2 pages.
Search Report for: Robot Collision Detection by John Johnson, dated Aug. 3, 2018, 4 pages.
Search Report for: Implant Trajectory and Tool Planning via Navigated Instrument by John Johnson, dated Aug. 9, 2018, 3 pages.
Search Report for: Improved Low-Contrast CBCT Imaging by John Johnson, dated Aug. 6, 2018, 3 pages.
Allowed Claims, showing Amendments to the claims for U.S. Patent Application Publication No. 2009/0185655, 7 pages.
Allowed Claims, showing Amendments to the claims for U.S. Patent Application Publication No. 2016/0005194, 4 pages.
Patent Search for CBCT-fluoroscopy-radiography, Mar. 2, 2018.
Alk et al., "Smart Device Assisted Method for Rod Length and Rod Radius Measurement in Percutaneious Pedicle Screw Surgery", Prizeglad Elektrotechniczny, vol. 3, Mar. 5, 2016, pp. 30-33.
Andreas Alk et al: "Smart Device Assisted Method for Rod Length and Rod Radius Measurement in Percutaneous Pedicle Screw Surgery", Przeglad Elektrotechniczny, vol. 3, Mar. 5, 2016 (Mar. 5, 2016), pp. 30-33, XP055668769, PO ISSN: 0033-2097, DOI: 10.15199/48.2016.03.07.

* cited by examiner

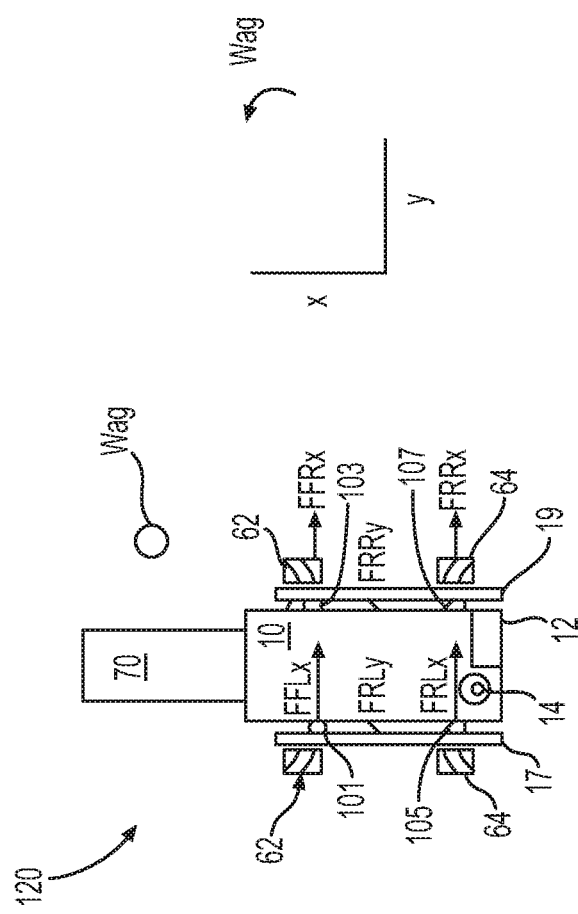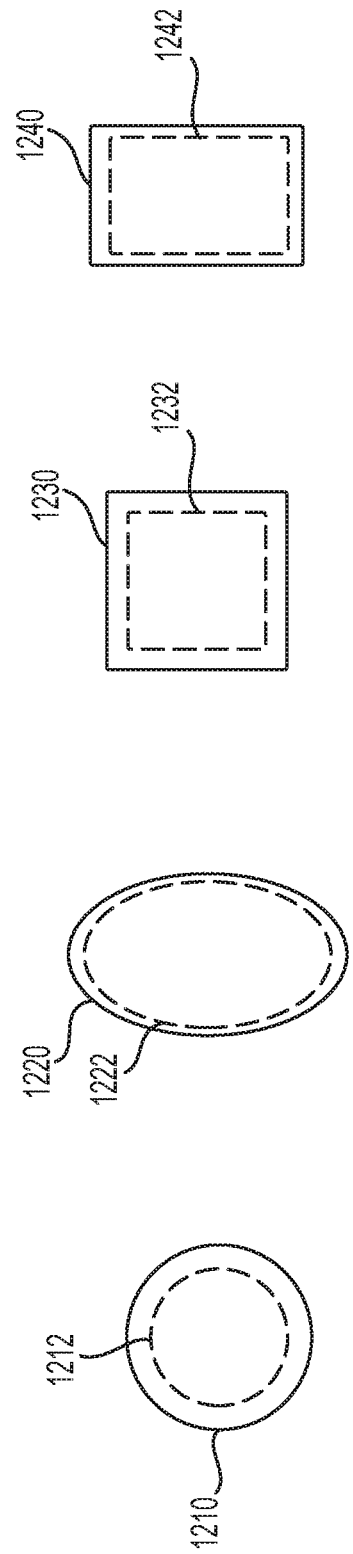

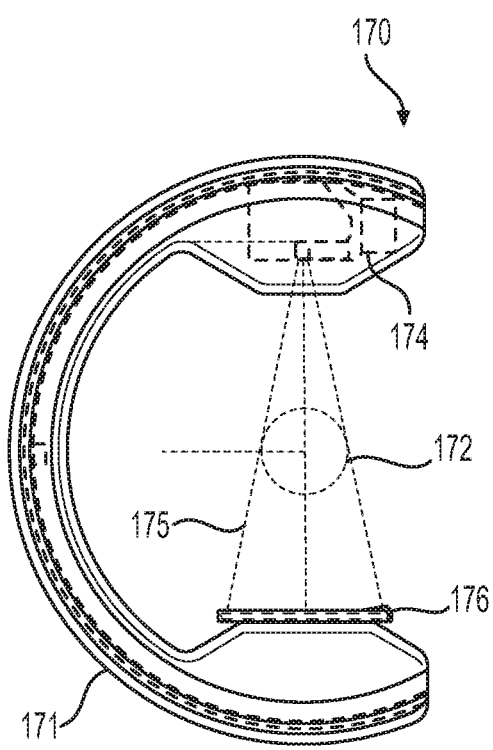
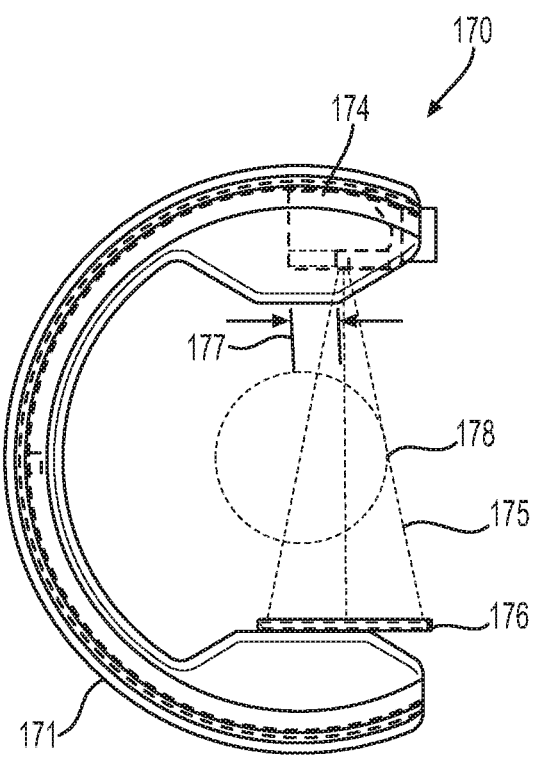
FIG. 17A  FIG. 17B
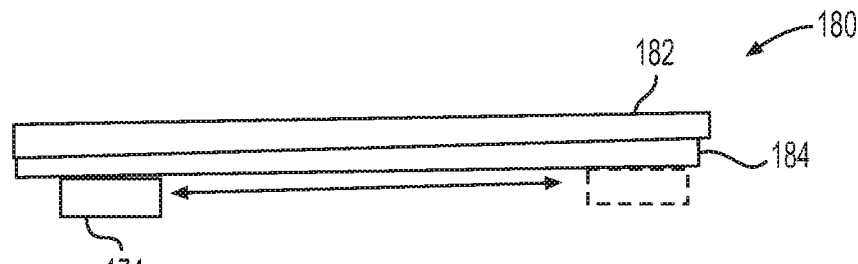
FIG. 18A
FIG. 18B

PORTABLE MEDICAL IMAGING SYSTEM AND METHOD

CROSS REFERENCE TO RELATED APPLICATION

This application is a continuation-in-part of U.S. patent application Ser. No. 15/180,126, filed on Jun. 13, 2016, which is a continuation-in-part of U.S. patent application Ser. No. 15/014,083, filed Feb. 3, 2016. These priority applications are hereby incorporated by reference in the entirety for all purposes.

TECHNICAL FIELD

The present disclosure relates to medical imaging systems, and more particularly, controlled movement of the imaging system or components thereof.

BACKGROUND OF THE DISCLOSURE

Healthcare practices have shown the tremendous value of three-dimensional imaging such as computed tomography (CT) imaging, as a diagnostic tool in the Radiology Department. These imaging systems generally contain a fixed bore into which the patient enters from the head or foot. Other areas of care, including the operating room, intensive care departments and emergency departments, rely on two-dimensional imaging (fluoroscopy, ultrasound, 2-D mobile X-ray) as the primary means of diagnosis and therapeutic guidance.

While mobile solutions for 'non-radiology department' and patient-centric 3-D imaging do exist, they are often limited by their freedom of movement to effectively position the system without moving the patient. Their limited freedom of movement has hindered the acceptance and use of mobile three-dimensional imaging systems.

Therefore, there is a need for a small scale and/or mobile three-dimensional imaging systems for use in the operating room, procedure rooms, intensive care units, emergency departments and other parts of the hospital, in ambulatory surgery centers, physician offices, and the military battlefield, which can access the patients in any direction or height and produce high-quality three-dimensional images. These imaging systems may include intra-operative CT and magnetic resonance imaging (MRI) scanners, robotic systems to aid in their use or movement. These include systems with 180-degree movement capability ("C-arms") and may also include imaging systems with 360-degree movement capability ("O-arms").

These systems may be very useful during surgery or other procedures when a real-time image is desired to guide operating room personnel. One issue during imaging is the precise positioning of the imaging system. This is especially important in an operating room or operating theatre, in which the size and weight of the imaging equipment and the presence of numerous required personnel make it difficult to precisely position the imaging equipment.

SUMMARY OF THE DISCLOSURE

A method for imaging using a portable medical imaging system having an imaging signal transmitter and an imaging sensor is disclosed. The method includes positioning the imaging signal transmitter and the imaging sensor generally opposite to one another and facing a point therebetween. The imaging sensor defines an angle of incidence with respect to a signal emitted from the imaging signal transmitter. The method also includes recording a first signal from the imaging signal transmitter using the imaging sensor, so as to capture an image of a first portion of a field-of-view, rotating the imaging sensor about the point such that the angle of incidence changes, and recording a second signal from the imaging signal transmitter using the imaging sensor, so as to capture an image of a second portion of the field-of-view.

A portable medical imaging system is disclosed. The system includes a movable station having a movable C-arm. The system also includes an imaging signal transmitter attached to the movable C-arm, and an imaging sensor positioned generally opposite to the imaging signal transmitter and attached to the movable c-arm. The imaging sensor is configured to rotate relative to a point approximately on a center axis of the movable C-arm independently of the imaging signal transmitter, so as to change an angle of incidence for a signal transmitted from the imaging signal transmitter to the imaging sensor, and provide a field-of-view that is larger than the field-of-view of the imaging sensor at a single position.

A portable medical imaging system is disclosed. The system includes a movable station, a gantry mount attached to the movable station, a gantry rotatably attached to the gantry mount and including a first C-arm slidably mounted to and operable to slide relative to the gantry mount, a second C-arm slidably coupled to the first C-arm, the first and second C-arms together providing a 360 degree rotation about an object to be imaged, and a control system for controlling motion of the movable station and first and second C-arms, and for controlling imaging of the portable imaging system. The control system is configured to cause the portable medical imaging system to perform operations, the operations including positioning the imaging signal transmitter and the imaging sensor generally opposite to one another and facing a point therebetween. The imaging sensor defines an angle of incidence with respect to a signal emitted from the imaging signal transmitter. The operations also include recording a first signal from the imaging signal transmitter using the imaging sensor, so as to capture an image of a first portion of a field-of-view. The operations further include rotating the imaging sensor about the point such that the angle of incidence changes, and recording a second signal from the imaging signal transmitter using the imaging sensor, so as to capture an image of a second portion of the field-of-view.

The disclosure includes many aspects and embodiments, of which only a few are described in the specification and drawings below.

BRIEF DESCRIPTION OF DRAWINGS

FIG. 10 is a top plan view of a portable medical imaging device equipped with the control system and omni-directional wheels ("omni-wheels") of the present disclosure and depicting a first example of an array of sensors.

FIGS. 12A-12D depict arrays of sensors useful in portable medical imaging equipment.

FIGS. 17A-17B depict another embodiment in which the imaging signal transmitter and imaging signal sensor have another translational degree of freedom.

FIGS. 18A-18B depict additional details that allow the additional degree of freedom.

DETAILED DESCRIPTION

For purposes of this application, the terms "code", "software", "program", "application", "software code", "software module", "module" and "software program" are used interchangeably to mean software instructions that are executable by a processor. A "user" can be a physician, nurse, or other medical professional.

Figure 1:
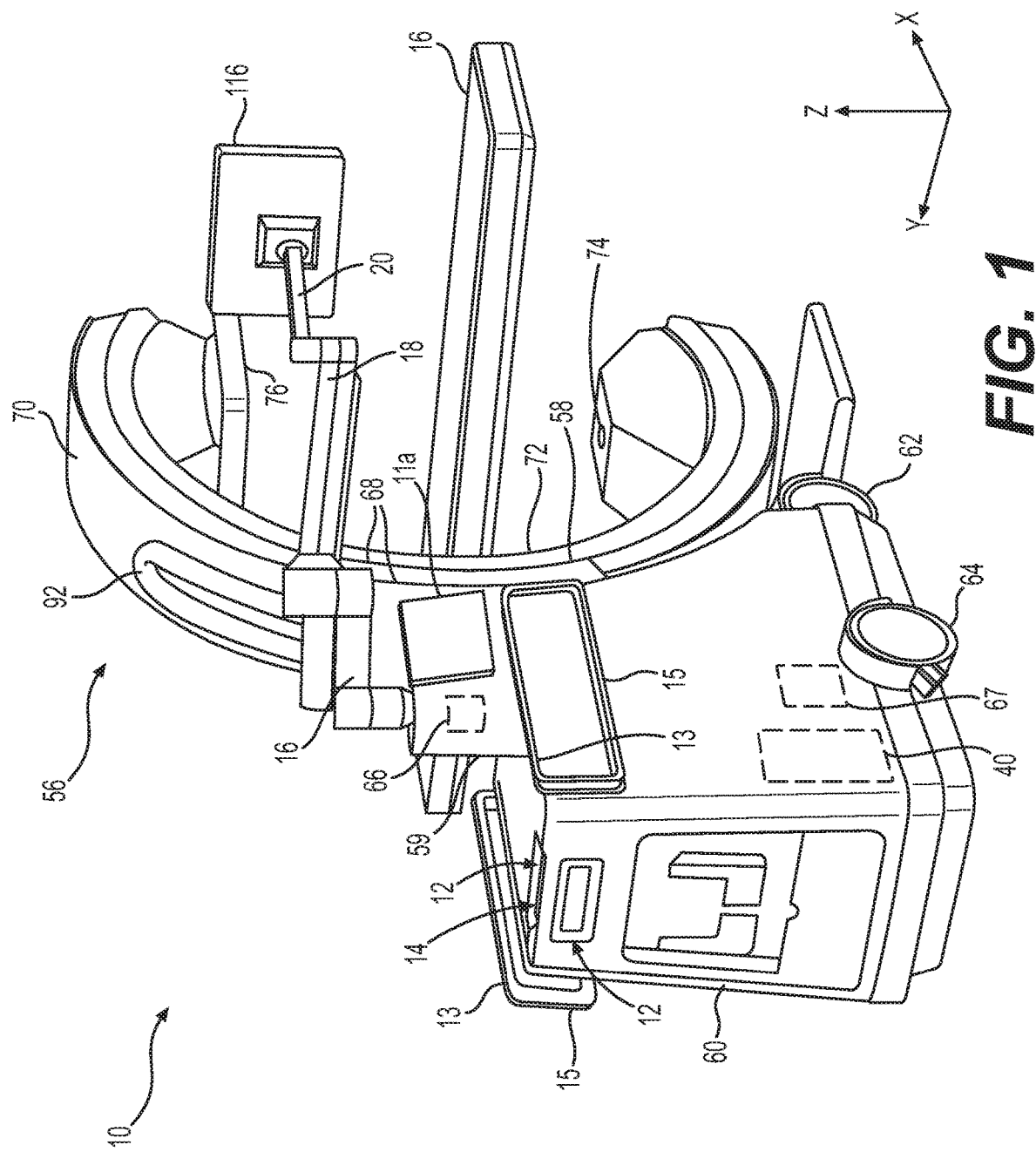
FIG. 1 is a perspective rear view of an imaging system according to one embodiment of the present disclosure.

Turning now to the drawing, FIG. 1 is a schematic diagram showing an imaging system 10, such as a computerized tomographic (CT) x-ray scanner, in accordance with one embodiment of the disclosure. The imaging system 10 includes a movable station 60 and a gantry 56. The movable station includes a vertical shaft 59 and a gantry mount 58 which is rotatably attached to the vertical shaft. The movable station 60 includes two front omni-directional wheels 62 and two rear omni-directional wheels 64, which together provide movement of the movable station 60 in any direction in an X-Y plane. The horizontal X-Y plane is depicted in the Cartesian coordinate system X, Y axes shown in FIG. 1, along with a vertical axis Z. The omni-directional wheels 62, 64 can be obtained, for example, from Active Robots Limited of Somerset, U.K. A pair of handles 15 mounted to the housing of the movable station 60 allow a user to manually maneuver the station.

A motor 66 attached to the vertical shaft 59 is designed to rotate the gantry mount 58 full 360 degrees about the X-axis and a motor 67 moves the gantry mount 58 vertically along the z-axis under the control of the motion control module 51.

The gantry 56 includes a first C-arm 70 slidably coupled to the gantry mount 58 and a second C-arm 72 which is slidably coupled to the first C-arm. In the embodiment shown, the first and second C-arms 70, 72 are outer and inner C-arms, respectively. In the embodiment shown, the outer and inner C-arms 70, 72 are partially-circular in shape and rotate circumferentially about a central axis so as to allow imaging of a patient who is lying in bed 26 without the need to transfer the patient.

An imaging signal transmitter 74 such as an X-ray beam transmitter is mounted to one side of the second C-arm 72 while an imaging sensor 76 such as an X-ray detector array is mounted to the other side of the second C-arm and faces the transmitter. In this example, X-ray transmitter 74 transmits an X-ray beam which is received by X-ray detector or receiver 76 after passing through a relevant portion of a patient (not shown).

In one embodiment, the system 10 is a multi-modality x-ray imaging system designed with surgery in mind. Imaging modalities include, but are not limited to, fluoroscopy, 2D Radiography, and Cone-beam CT. Fluoroscopy is a medical imaging technique that shows a continuous X-ray image on a monitor, much like an X-ray movie. 2D Radiography is an imaging technique that uses X-rays to view the internal structure of a non-uniformly composed and opaque object such as the human body. CBCT (cone beam 3D imaging or cone beam computer tomography) also referred to as C-arm CT, is a medical imaging technique consisting of X-ray computed tomography where the X-rays are divergent, forming a cone. Magnetic resonance imaging (MRI) may also be employed, with suitable precautions for using powerful magnets and controlling the magnetic fields they generate.

The movable station 60 includes an imaging controller system 40 which serves a dual function of (1) controlling the movement of the omni-directional wheels 62, 64, gantry mount 58 and the gantry 56 to position the imaging signal transmitter 74 in relation to the patient, and other component movements as needed, and (2) controlling imaging functions for imaging the patient once proper positioning has been achieved.

Figure 2:
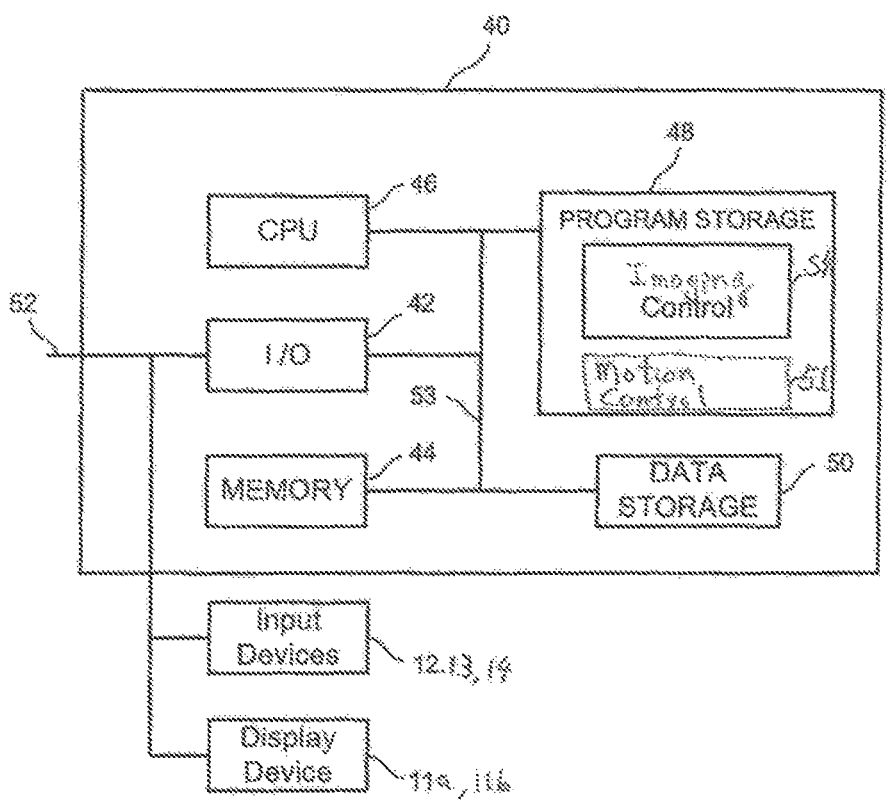
FIG. 2 is a schematic diagram of an imaging controller system 40 according to one embodiment of the present disclosure.

Referring now to FIG. 2, the imaging controller system 40 of the present disclosure is connected to a communication link 52 through an I/O interface 42 such as a USB (universal serial bus) interface, which receives information from and sends information over the communication link 52. The imaging controller system 40 includes memory storage 44 such as RAM (random access memory), processor (CPU) 46, program storage 48 such as ROM or EEPROM, and data storage 50 such as a hard disk, all commonly connected to each other through a bus 53. The program storage 48 stores, among others, imaging control module 54 and motion control module 51, each containing software to be executed by the processor 46. The motion control module 51 executed by the processor 46 controls the wheels 62, 64 of the movable station 60 and various motors in the gantry mount 58 and gantry 56 to position the station 60 near the patient and position the gantry in an appropriate position for imaging a relevant part of the patient. The motion control module may also control additional components used for positioning, as explained below.

The imaging control module 54 executed by the processor 46 controls the imaging signal transmitter 74 and detector array 76 to image the patient body. In one embodiment, the imaging control module images different planar layers of the body and stores them in the memory 44. In addition, the imaging control module 54 can process the stack of images stored in the memory 44 and generate a three dimensional image. Alternatively, the stored images can be transmitted to a host system (not shown) for image processing.

The motion control module 51 and imaging control module 54 include a user interface module that interacts with the user through the display devices 11a and 11b and input devices such as keyboard and buttons 12 and joystick 14. Strain gauges 13 mounted to the handles 15 are coupled to the I/O device 42 and conveniently provide movement of the movable station 60 in any direction (X, Y, Wag) while the user is holding the handles 15 by hand, as will be discussed in more detail below. The user interface module assists the user in positioning the gantry 56. Any of the software program modules in the program storage 48 and data from the data storage 50 can be transferred to the memory 44 as needed and is executed by the CPU 46. The display device 11a is attached to the housing of the movable station 60 near the gantry mount 58 and display device 11b is coupled to the movable station through three rotatable display arms 16, 18 and 20. First display arm 16 is rotatably attached to the movable station 60, second display arm 18 is rotatably attached to the first arm 16 and third display arm 20 is rotatably attached to the second display arm. The display devices 11a, 11b can have touch screens to also serve as input devices through the use of user interface modules in the modules 51 and 54 to provide maximum flexibility for the user.

Navigation markers 68 placed on the gantry mount 58 are connected to the imaging controller system 40 through the link 52. Under the control of the motion control module 51, the markers 68 allow automatic or semi-automatic positioning of the gantry 56 in relation to the patient bed or OR (operating room) table via a navigation system (not shown). The markers 68 can be optical, electromagnetic or the like. They may also be placed on other convenient and useful places, e.g., on the patient bed, or otherwise, so that the marker or markers will be visible in the images taken and may be used to orient connecting images when more than one image is taken of a patient, or other object to be imaged. The markers may also contribute to merging or coordinating multiple images when more than one image is taken.

Information can be provided by the navigation system to command the gantry 56 or system 10 to precise locations. In one example, a surgeon holds a navigated probe at a desired orientation for the imaging system 10 to acquire a fluoroscopic or radiographic image along that specified trajectory. Advantageously, this will remove the need for scout shots thus reducing x-ray exposure to the patient and operating room (OR) staff. The navigation markers 68 on the gantry 56 will also allow for automatic registration of 2D or 3D images acquired by the system 10. The markers 68 will also allow for precise repositioning of the system 10 in the event the patient has moved. The markers may be radiopaque or made from other material that makes coordination or navigation easy for the imaging specialists or other medical professionals. The navigation probes or markers may be placed as desired, e.g., nearby or on the object to be imaged, so that the markers do not interfere with the imaging or its interpretation.

In the embodiment shown, the system 10 provides a large range of motion in the 6-degrees of freedom ("DOF") described below. Under the control of the motion control module 51, there are two main modes of motion: positioning of the movable station 60 and positioning of the gantry 56. Other positioning modes are described and may also be included.

The movable station 60 positioning is accomplished via the four omni-directional wheels 62, 64. These wheels 62, 64 allow the movable station 60 to be positioned in all three DOF about the horizontal plane (X, Y, Wag). "Wag" is a system 10 rotation about the vertical axis (Z-axis), "X" is a system forward and backward positioning along the X-axis, and "Y" is system 10 lateral motion along the Y-axis. Under the control of the control module 51, the system 10 can be positioned in any combination of X, Y, and Wag (Wag about any arbitrary Z-axis due to use of omni-directional wheels 62, 64) with unlimited range of motion. In particular, the omni-directional wheels 62, 64 allow for positioning in tight spaces, narrow corridors, or for precisely traversing up and down the length of an OR table or patient bed.

The gantry 56 positioning is accomplished about (Z, Tilt, Rotor). "Z" is gantry 56 vertical positioning, "Tilt" is rotation about the horizontal axis parallel to the X-axis as described above, and "Rotor" is rotation about the horizontal axis parallel to the Y-axis as described above.

Together with the movable station 60 positioning and gantry 56 positioning, the system 10 provides a range of motion in six DOF (X, Y, Wag, Z, Tilt and Rotor) to place the movable station 60 and the imaging transmitter 74 and sensor 76 precisely where they are needed. Advantageously, 3-D imaging can be performed regardless of whether the patient is standing up, sitting up or lying in bed and without having to move the patient.

Precise positions of the system 10 can be stored in the storage memory 50 and recalled at any time by the motion control module 51. This is not limited to gantry 56 positioning but also includes system 10 positioning due to the omni-directional wheels 62, 64, and other axes of motion, as described below.

Figure 3:
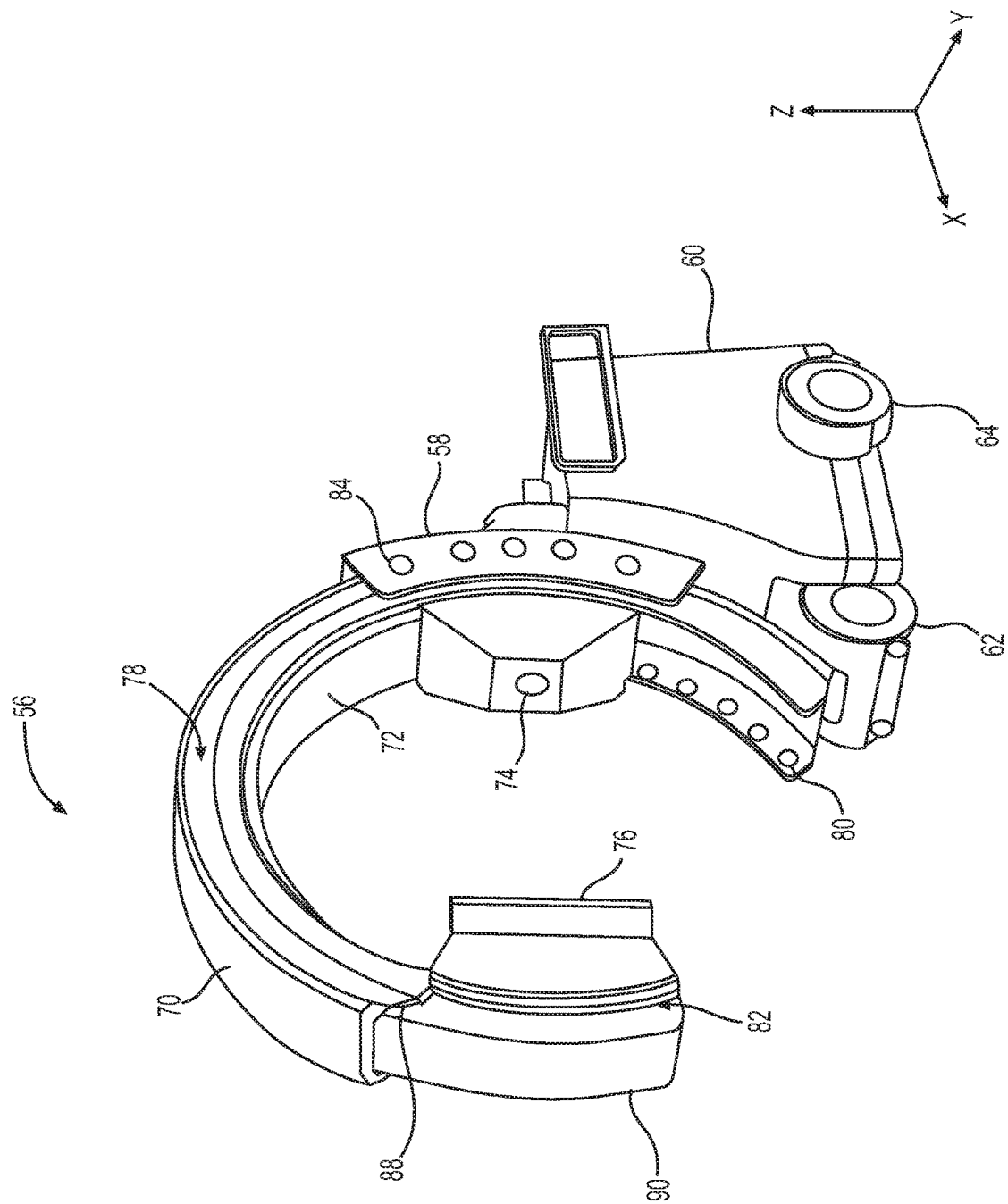
FIG. 3 is a perspective front view of the imaging system of FIG. 1.

As shown in FIG. 3, each of the gantry mount 58, outer C-arm 70 and inner C-arm 72 respectively has a pair of side frames 86, 88, 90 that face each other. A plurality of uniformly spaced rollers 84 are mounted on the inner sides of the side frames 86 of the gantry mount 58. The outer C-arm 70 has a pair of guide rails 78 on the outer sides of the side frames 88. The rollers 84 are coupled to the guide rails 78. As shown, the rollers 84 and the guide rails 78 are designed to allow the outer C-arm 70 to telescopically slide along the gantry mount 58 so as to allow at least 180 degree rotation of the C-arm about its central axis relative to the gantry mount.

A plurality of uniformly spaced rollers 80 are mounted on the inner sides of the side frames 88 of the outer C-arm 70. The inner C-arm 70 has a pair of guide rails 82 on the outer sides of the side frames 90. The rollers 80 are coupled to the guide rails 82. As shown, the rollers 80 and the guide rails 82 are designed to allow the inner C-arm 72 to telescopically slide along the outer C-arm 70 so as to allow at least 180 degree rotation of the C-arm about its central axis relative to the outer C-arm.

Thus, the present disclosure as disclosed herein advantageously allows the gantry 56 to rotate about its central axis a full 360 degrees to provide the maximum flexibility in positioning the imaging system 10 with minimum disturbance of the patient.

Figure 5:
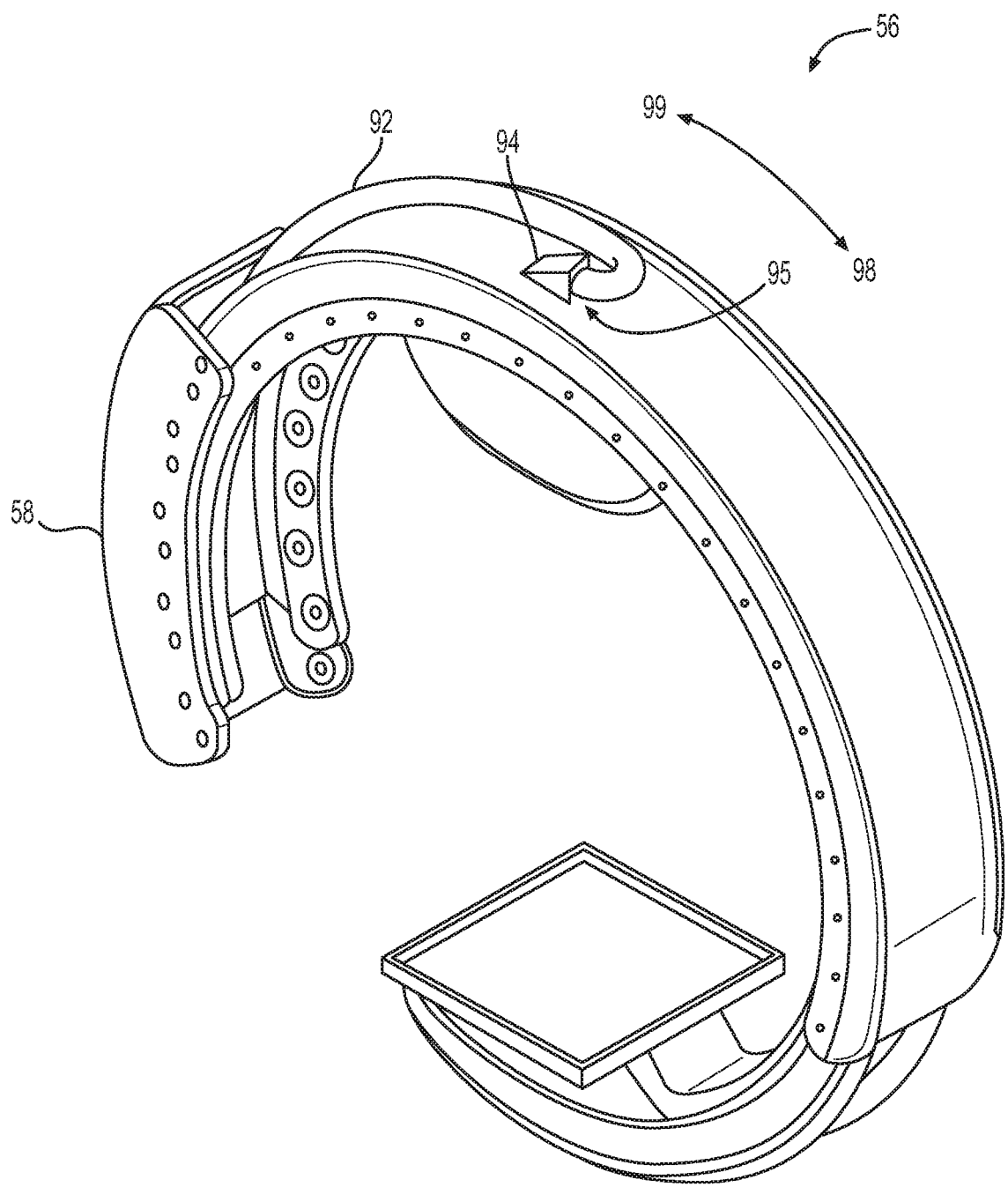
FIG. 5 is a perspective view of the gantry partially showing a cabling arrangement.
Figure 6:
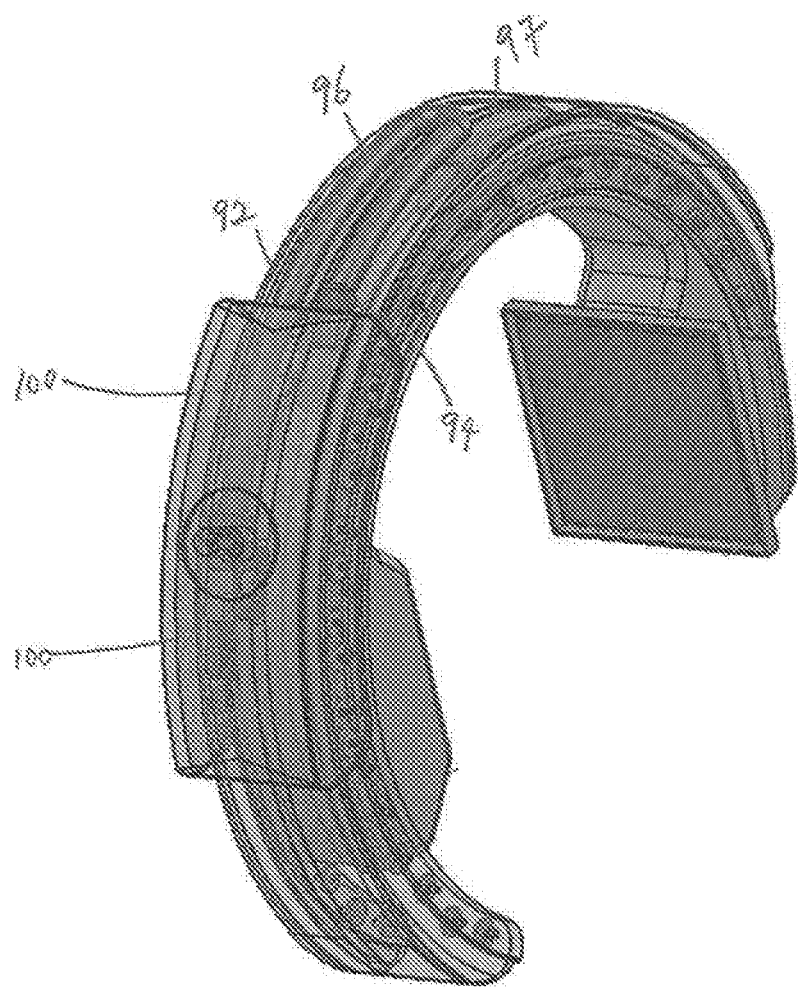
FIG. 6 is a perspective view of the gantry showing the cabling arrangement.
Figure 7:
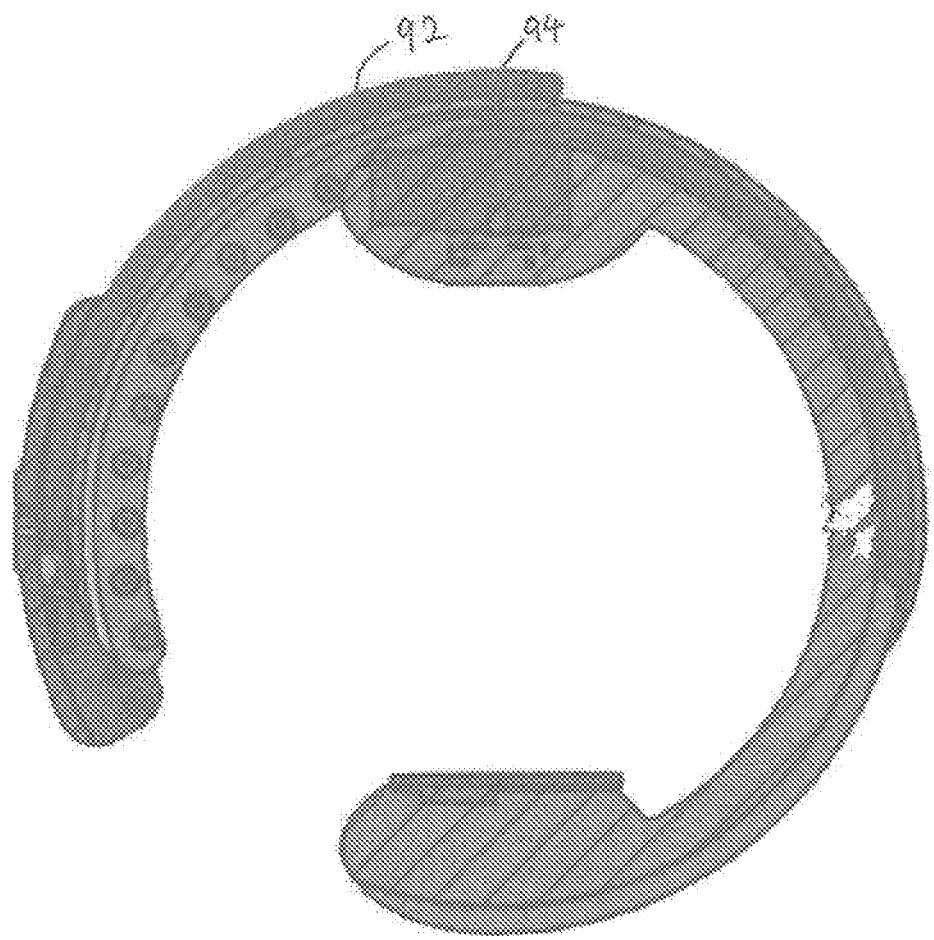
FIG. 7 is a side view of the gantry showing the cabling arrangement.

In another aspect of the present disclosure, a unique cabling arrangement is provided to make the imaging system 10 more compact and visually more appealing. As shown in FIGS. 5 and 6, a cable carrier/harness 92 contains electrical cables to carry signals between the imaging controller system 40 and various motors, X-ray transmitter 74, imaging sensor or detector 76 and various electronic circuits in the gantry 56. A first cable router 94 is mounted to the outer surface of the outer C-arm 70 and a second cable router 96 is mounted to the outer surface of the inner C-arm 72. Each cable router 94, 96 has a through-hole 95, 97 through which the cable carrier 92 passes.

The cable carrier 92 extends from the gantry mount 58 over the outer surface of the first C-arm 70, through the through-hole 95 of the first cable router 94 and over an outer surface of the second C-arm 72. The cable carrier 92 overlying the first C-arm 70 extends in a first circumferential direction (clock-wise as shown) 98 and enters the first cable router 94 in a second circumferential direction (counter clock-wise as shown) 99 opposite to the first circumferential direction to create a 180 degree service loop over the outer surface of the first C-arm.

From there, the cable carrier 92 extends in the first circumferential direction 98 and enters the second cable router in the second circumferential direction 99 to create another service loop over the outer surface of the second C-arm 72.

The particular locations of the first and second cable routers 94, 96 combined with the service loops allow slack in the cable carrier 92 to provide the gantry 56 with full 360 degrees rotation without tangling or causing stress in the cable carrier. In the embodiment shown, the routers are mounted near the midpoint of the C-arms.

Figure 8:
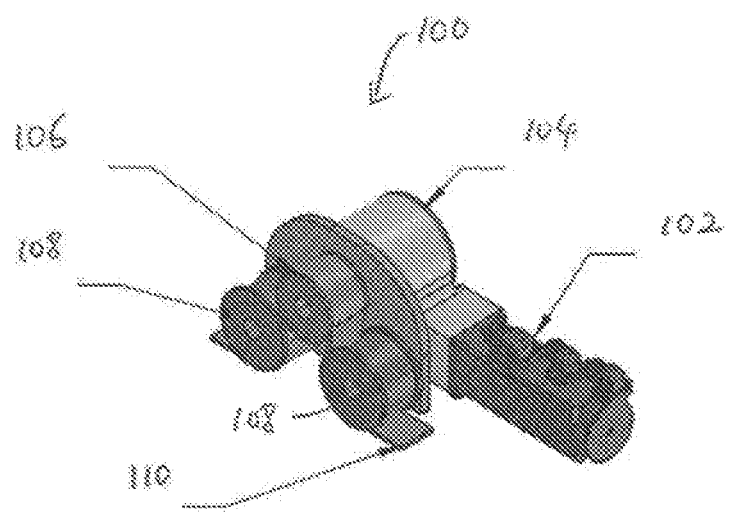
FIG. 8 illustrates a motor assembly for telescopically controlling the C-arms of the gantry.

FIG. 8 illustrates one embodiment of a motor assembly 100 useful for telescopically rotating the outer C-arm 70 relative to the gantry mount 58 and for rotating the inner C-arm 72 relative to the outer C-arm. Each motor assembly 100 includes a servo motor 102 with encoder feedback, gear box 104 to change the turning ratio, drive pulley 106, idler pulleys 108 and belt 110 threaded between the drive pulley and the idler pulleys. One motor assembly 100 is mounted to the gantry mount to move the outer C-arm 70 relative to the gantry mount and another motor assembly is mounted to the outer C-arm 70 near the center of the arm to move the inner C-arm 70 relative to the outer C-arm.

Figure 9A:
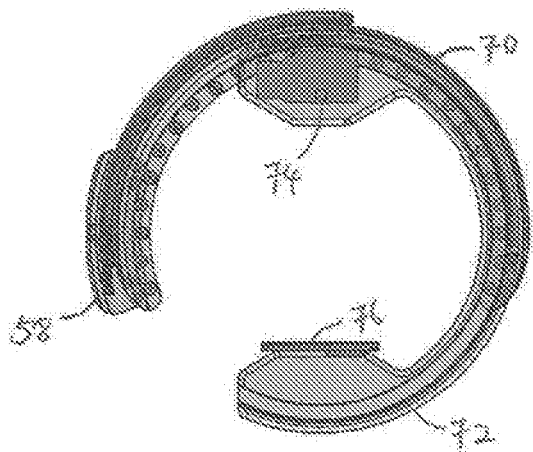
FIGS. 9A-9G illustrate the 360-degree rotation of the gantry in 60 degree increments.
Figure 9B:
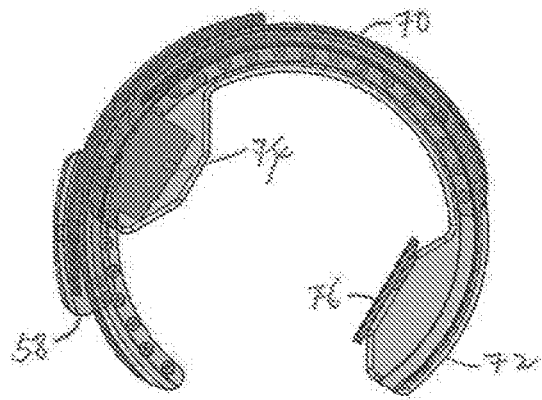
Figure 9C:
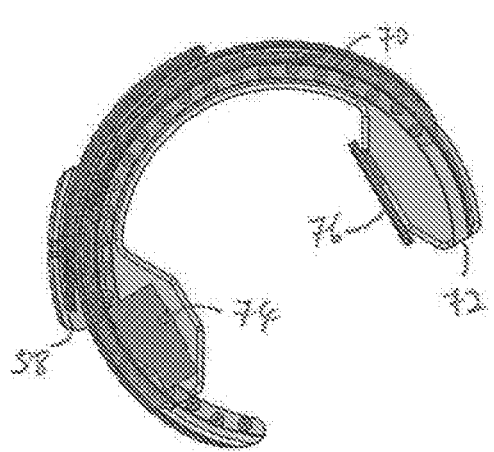
Figure 9D:
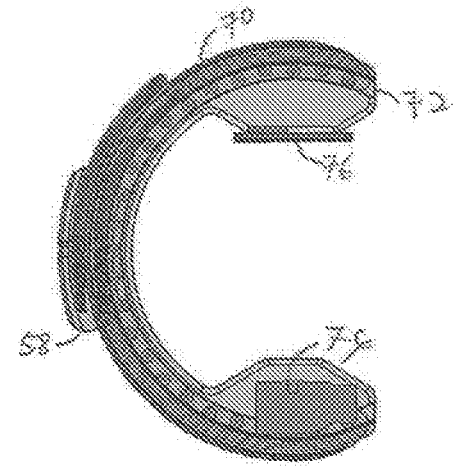
Figure 9E:
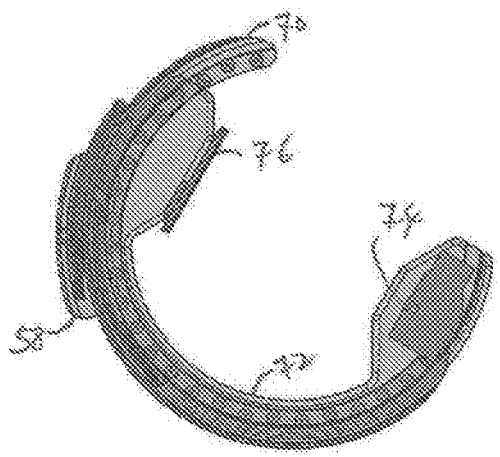
Figure 9F:
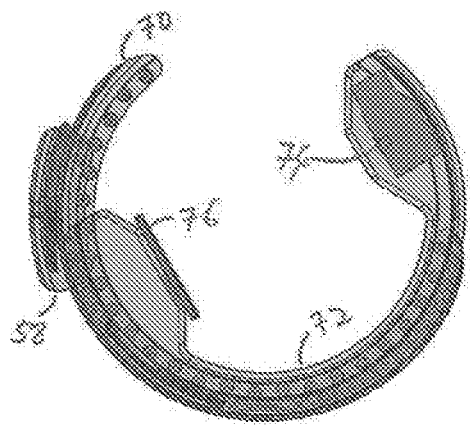
Figure 9G:
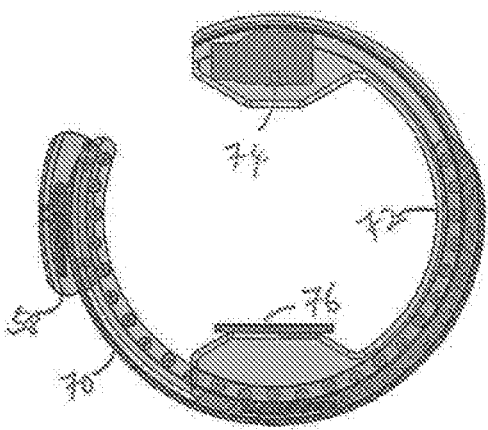

FIGS. 9A-9G illustrate the 360 degree rotation of the gantry 56 in the counter-clockwise direction in 60 degree increments, with FIG. 9A representing a zero degree position of the imaging sensor 76 and transmitter 74. FIG. 9B represents a 60 degree turn/position of the gantry 56. For each 60 degree turn of the gantry 56, the motor assemblies 100, under the control of the motion control module 51, turn the inner C-arm 72 by 30 degrees counter-clock wise and also turn the outer C-arm 70 by 30 degrees counter-clock wise for a combined 60 degree turn. FIG. 9G represents a full 360 degree turn of the gantry 56. As can be seen, the outer C-arm 70 and inner C-arm 72 have each moved 180 degrees from the original zero degree position of FIG. 9A. Note that the transmitter 74 and sensor 76 in FIGS. 9D and 9G are reversed from their positions in FIGS. 1 and 9A. This may be advantageous, for example, if there is an advantage in having the transmitter on one particular side or in having the sensor on one particular side. These orientations are made possible and facile with the present disclosure.

As described above in detail, the present disclosure in various embodiments provide the following benefits: (1) movement of the system in any X-Y direction with Wag-rotation about any Z-axis using omni-directional wheels 62, 64; (2) double telescoping C-gantry for full 360-degree imaging beam rotation; (3) imaging while lying in bed, sitting or standing such as standing CBCT; (4) storage and recall of system 10 and gantry 56 positions; (5) quasi-simultaneous multi-planar x-ray imaging; and (6) recall of positions via robotics or navigation coordinates.

The control system for the portable medical imaging system was described above in FIG. 2. The control system for the sensor-controlled movement of the portable medical imaging system is further explained here with reference to FIG. 2 and FIG. 10. Imaging controller system 40 includes both a motion control module 51 and an imaging control module 54. Input devices may include a keyboard with function keys 12, handles 13 and a joystick 14. Any of these input devices may control either or both of the motion control module 51 and the imaging control module 54. Switching between a motion control mode and an imaging control mode may be accomplished by a function key, a touch screen command from one of the display devices, or other desired method. The portable medical imaging system may also include, as part of the motion control module 51 or the input/output 42 a smart phone or cellular phone link or global positioning system (GPS) that may be useful for communicating information concerning a position of the patient or the imaging system via communication link 52.

Control system 120 of FIG. 10 is depicted as a plan view of the portable imaging control system 120, depicting a top view of the imaging system 10 and first C-arm 70. Omni-wheels 62, 64 are separated into front portion omni-wheels 62, left and right, and rear portion omni-wheels 64, also left and right. FIG. 10 also depicts the three axes for the three degrees of omni-wheel freedom of motion of the system. As depicted in the figure, these include freedom to move left or right along a y-axis, freedom to move forward and backward along an x-axis, and freedom of rotation along a rotational axis Wag that is perpendicular to a plane formed by the x and y axes, i.e., a vertical axis. Thus, the vertical axis Wag in FIG. 10 is perpendicular to the plane of the drawing. The vertical rotational axis may be placed as desired with respect to the imaging system since no physical axis of rotation is required. For example, one may program the program storage 48 so that rotational axis Wag coincides with a vertical axis of shaft 59 or the vertical axis of joystick 14. An alternative convenient placement may be the geometrical center of the movable station 60 (see FIG. 1) or a corner of the top of the movable station. Any convenient and useful placement of the axis may be made.

FIG. 10 may also provide a useful reference for a discussion of the sensors used in this disclosure. Left sensors 101, 105 are mounted on the left handle 17 while right sensors 103 and 107 are mounted on the right handle 19. A first embodiment may include these four sensors 101, 103, 105, 107, as shown. A person, such as a health care professional operating the portable imaging system 10, may position the device by using the handles 17, 19 and the motion control module 51. In one embodiment, the motion control may have two modes, a transport mode and a fine-tune mode. For example, if the portable medical imaging device 10 is transported from one wing of a hospital or other health-care facility, speed may be more highly valued than fine-tuned positioning. Thus, pushing on the rear portion handles 17, 19 of imaging system 10 may activate the transport mode. Pushing on either of the two handles 17, 19 may activate a fine-tune mode, in which every movement of the omni-wheels 62, 64 is slower and more deliberate. Switching between these modes may also be accomplished by appropriate programming allowing the user to switch via a function key, a command, a touch-screen input, and so forth.

In fine tune mode, motion control 51 may be used to return the imaging system 10 to a set position, e.g., snap to a predetermined position. For example, and with reference to FIG. 1, if an imaging session has concluded, the user may wish to move the imaging system 10 to a left-most position with respect to patient bed 26. The position may be programmed into the motion control 51 and may require movement in both the x and y directions, per the axes depicted in FIGS. 1 and 10. This may be accomplished using the keyboard or function buttons 12 available to the operator, the touch screens of the display devices 11a, 11b, a joystick 14 or a predetermined applied force and direction to the handles 17, 19. The keyboard, the function buttons and the touch screen display devices may also be used to control the imaging and motion control portions, including the omni-directional wheels 62, 64.

The capabilities of the omni-wheels 62, 64 may also be used so that the system rotates the portable imaging system 10 about a specified vertical axis. This may be any convenient axis, such as a geometrical center of the imaging system 10, a particular feature or part of the imaging system 10 or its cart, a feature of a robot mounted on the imaging system, and so forth. The motion applied by the omni-wheels 62, 64 may also be proportional to the force(s) applied to the sensor(s) 101, 103, 105, 107—a light force may result in slower, more deliberate speed while a higher force or heavier touch may result in higher speeds applied by the omni-wheels 62, 64. In addition, the direction in which the forces are applied may indicate the desired direction of movement of the portable imaging system 10. The forces applied to the sensor(s) 101, 103, 105, 107 are resolved by motion control 51 into a resultant vector and moment that is used to drive each of front wheels 62 and rear wheels 64, as needed, to provide the desired motion.

We now discuss examples of movement using FIG. 10. In one example, pushing the left handle 17 forward would operate to cause the device to go forward and turn the device to the right. In another example, pushing the left handle 17 activates sensors 101, 105 to require forward movement. The sensor(s) 101, 103, 105, 107 may be strain gauges that interpret the force as applied in a particular direction for sensors 101, 105, forward, but with no force applied to sensors 103, 107. Since no force is applied to the right handle 19 and its sensors 103, 107, motion control 51 interprets the signals from the sensors 103, 107 as calling for a right turn with only a slight forward motion. Thus, the portable imaging system 10 makes a tight turn to the right with minimal forward movement via the omni-wheels 62, 64. In embodiments, all four wheels 62, 64 may move in this example to achieve a slight rightward turn movement. The wheels 62, 64 may be controlled individually so that their movements together achieve a desired movement of the movable station 60. As discussed above, this is an example of movement in a fine-tune mode. In other embodiments, only the left wheels 62, 64 may be activated or only the right wheels 62, 64, depending on the desired movement.

In another example, pushing left handle 17 to the right applies a force to sensors 101, 105, calling for rightward lateral or side movement. If no forward or backward force is applied to the sensors 101, 105 and no force is applied to right sensors 103, 107, motion control 51 interprets the signals as calling for rightward lateral movement with no forward or backward motion, still in a fine-tune mode. Accordingly, all four omni-wheels 62, 64 may make a small movement in the direction indicated, i.e., a few mm or inches to the right. In another example, the front wheels 62 may turn in a forward and leftward direction while the rear wheels 64 turn backwards and to the right to achieve a left turn or rotation in position. In another example, pushing both handles 17, 19 to the left will bring up a transport mode rather than a fine-movement mode. This may cause the imaging system 10 to move to the left, e.g., as shown in FIG. 1, to a leftward position with respect to patient bed or table 26, which is not part of the portable imaging system 10. The same may be said for pushing both handles 17, 19 forward, in an x-axis direction, to move the cart forward, now in a transport mode rather than in a fine-tune mode. Although described with reference to applying a force to specific handles 17, 19 and sensors 101, 103, 105, 107, it will be appreciated that more or less handles and/or sensors may be employed with the system. In addition, different forces and/or movements may occur in a number of different configurations in order to employ the fine-tune and/or transport modes and/or to move the portable imaging system 10 about the operating room.

The sensors 101, 103, 105, 107 used in embodiments of the present disclosure may include a great many force sensors. These include strain gauges, force-sensing resistors, piezo-electric sensors, piezocapacitive pressure sensors, piezoresistors and microelectro-mechanical systems (MEMS) micro-scale strain gauges. Typically, a force sensor possesses an electrical property that is changed when a user applies a force to the sensor. The property may be an electrical conductance, a resistance or a capacitance that increases or decreases in a predictable manner when a force is applied. Piezo-type sensors may generate a small microvoltage when a pressure is applied. The sensor may be part of an electrical circuit for detecting such a change, e.g., a Wheatstone bridge. By using an array or plurality of strain gauges or sensors, the user may fine-tune the direction of the desired force to be applied to the omni-wheels.

Figure 11A:
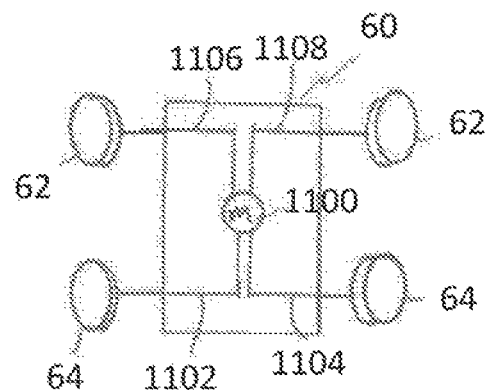
FIGS. 11A and 11B depict configurations for applying power to the omni-wheels of the portable station.
Figure 11B:
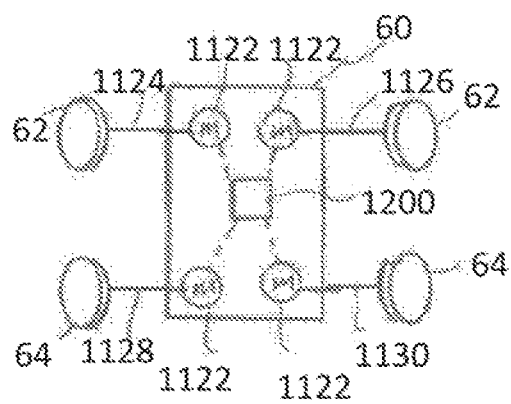

The sensors 101, 103, 105, 107 used in FIG. 10 and in the examples below may be used to control the wheels 62, 64 of the portable medical imaging device. Examples of such techniques are depicted in FIGS. 11A and 11B. In FIG. 11A, the movable station 60 is depicted with front wheels 62 and rear wheels 64, which may be the same or may be different. In this embodiment, motor 1100 under the direction of the motion control module 51, transmits power to each of the wheels as desired. The power supplied to the wheels 62, 64 may include manual operation, automatic operation, or a combination of both. The motor 1100 may have more than one shaft to supply power to axles 1102, 1104, 1106, 1108 to individually power the omni-wheels 62, 64. This allows for fine control of each wheel 62, 64 for precise placement of the portable imaging station and the imaging equipment mounted thereon. In one embodiment, the motor 1100 and each shaft or axle 1102, 1104, 1106, 1108 may further comprise a rotary encoder or other feedback mechanism to provide positional feedback to the motion control module.

Alternatively, as depicted in FIG. 11B, movable station 60 may include a local controller 1120 for allocating power via separate motors 1122 that power independent axles 1124, 1126, 1128, 1130 to each of the omni-wheels 62, 64. It may be simpler for motion control module 51 to maintain separate control of each omni-wheels 62, 64 via its own motor. In this embodiment, each motor 1122 may include its own encoder for positional feedback, and may also include an encoder or other feedback mechanism on axles 1124, 1126, 1128, 1130. Other methods for supplying power to the wheels 62, 64 may be used. The local controller or the motion control module may contain a computer program that resolves sensor readings into commands to each of the motors 1122 and axles 1124, 1126, 1128, 1130. With this technique, the omni-directional wheels 62, 64 are individually controlled for very accurate movement by the sensors provided. Feedback from the motion, such as from the rotary encoders on the axles 1124, 1126, 1128, 1130, or by other devices, can be used to store given positions for later use in restoring the movable station to a desired location.

The sensors 101, 103, 105, 107 used to sense a desired direction of the portable medical imaging system 10 may be mounted in the handles 17, 19, as disclosed above. The sensors 101, 103, 105, 107 may alternatively be mounted in a joystick or in other types of handles, as disclosed in FIGS. 12A-12D. A first alternate embodiment is disclosed in FIG. 12A. In this control system 1210, a plurality of force sensors 1212, six sensors, are mounted in a circular arrangement. A user presses on a surface of the control system, activating the sensors 1212 to guide the portable medical imaging system 10 in the appropriate direction. The direction is determined by the sensors 1212 that are activated and by the amount of force or pressure applied by the user. This is the same principle used in the example above of the handles 17, 19 of the portable imaging system 10. The circular control arrangement is useful for guiding the portable imaging device in all x-y directions, in a plane. Rotation about a predetermined axis may also be achieved by pushing up or down on the joystick or by commands to the keyboard or function button inputs. For example, depressing the joystick for a few seconds may command the portable medical imaging device to rotate clockwise about the axis, while pulling upwardly for a few seconds may command a counter-clockwise rotation.

Other examples with similar modes of operation are depicted in FIGS. 12B-12D. In FIG. 12B, eight sensors 1222 are arranged elliptically for a control system 1220 that is more suggestive of forward-backward movement, x-direction, as are the side handles discussed with respect to FIGS. 1 and 10. More sensors 1222 may be used for more sensitivity to the direction desired by the operator. In FIG. 12C, control system 1230 includes six force sensors 1232 mounted in a square pattern as shown, with two sensors 1232 for forward/backward movement and also with additional sensitivity for left/right or sideways direction with a four-corner distribution of the remaining four sensors 1232. FIG. 12D depicts an example of a control system 1240 configured with a plurality of sensors 1242 in a rectangular arrangement. This arrangement includes three sensors 1242 per side, allowing for finer tuning of lateral movements of the cart or imaging station. Other configurations may be used to guide the portable medical imaging system and its omni-directional wheels 62, 64.

Figure 13:
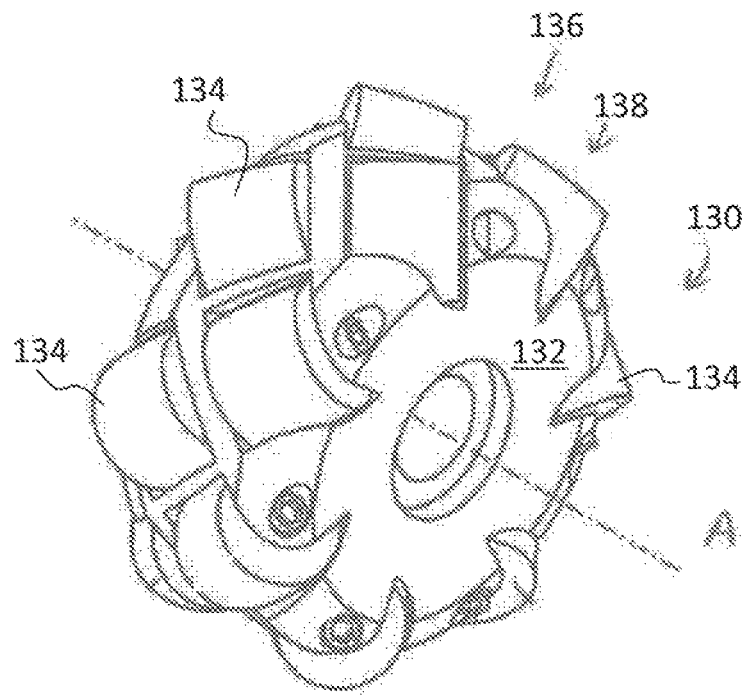
FIG. 13 is a perspective view of an example of a first omni-directional wheel ("omni-wheel") useful in imaging systems according to the present disclosure.

There are many types of omni-wheels 62, 64 useful in embodiments of the present disclosure, such as those depicted in FIGS. 13-16. Unlike traditional wheels, which only allow a device to move in one direction (e.g., forward and backward), the omni-directional wheels allow the portable imaging device to be moved in every direction (e.g., forward, backward, left, right, diagonally, in an arc, or the like). Thus, the omni-direction wheels 62, 64 allow the portable imaging device to be moved in any direction. Omni-directional wheels 62, 64 or Mecanum-type wheels generally have a central hub with a plurality of smaller wheels or rollers on its circumference. The smaller wheels are mounted at an angle to the central axis of the hub, such as 45 degrees or 90 degrees. FIG. 13 depicts an omni-directional wheel 130. This wheel 130 includes a central hub 132 about a central axis A, with a plurality of rollers or wheels 134 mounted in two non-coaxial rows 136, 138 at about a 45-degree angle to the central axis. The wheels or rollers 134 take turns being on the ground, making turning easier. These types of wheels 130 are described in U.S. Pat. Appl. 2010/0187779, which is hereby incorporated by reference in its entirety.

Figure 14:
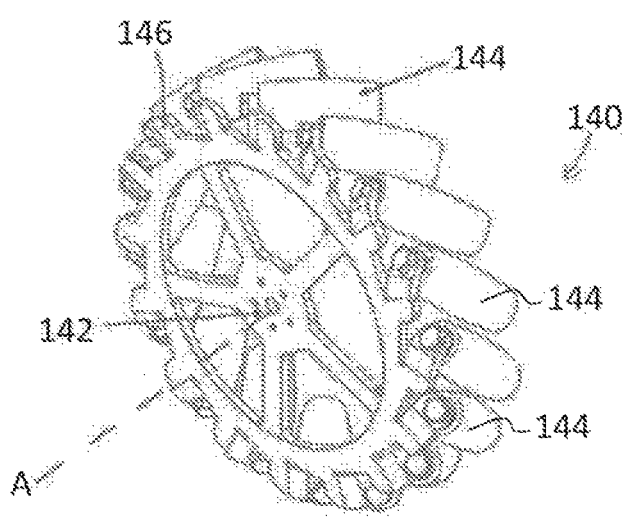
FIG. 14 is a perspective view of an example of a second omni-wheel useful in the present disclosure.

Another type of omni-directional wheel 62, 64 useful in the present disclosure is depicted in FIG. 14. Mecanum wheel 140 has a central hub 142 with a central axis A. A plurality of rollers 144 are mounted on flanges 146 on the periphery of the central hub. In this example, the flanges 146 are bent at about a 45-degree angle and thus the rollers 144 are also mounted at about a 45-degree angle to the central axis. Other angles may be used. Each wheel 62, 64 may be powered individually to guide the portable medical imaging cart in the desired direction. These types of wheels 140 are described in U.S. Pat. Appl. 2013/0292918, which is hereby incorporated by reference in its entirety.

Figure 15:
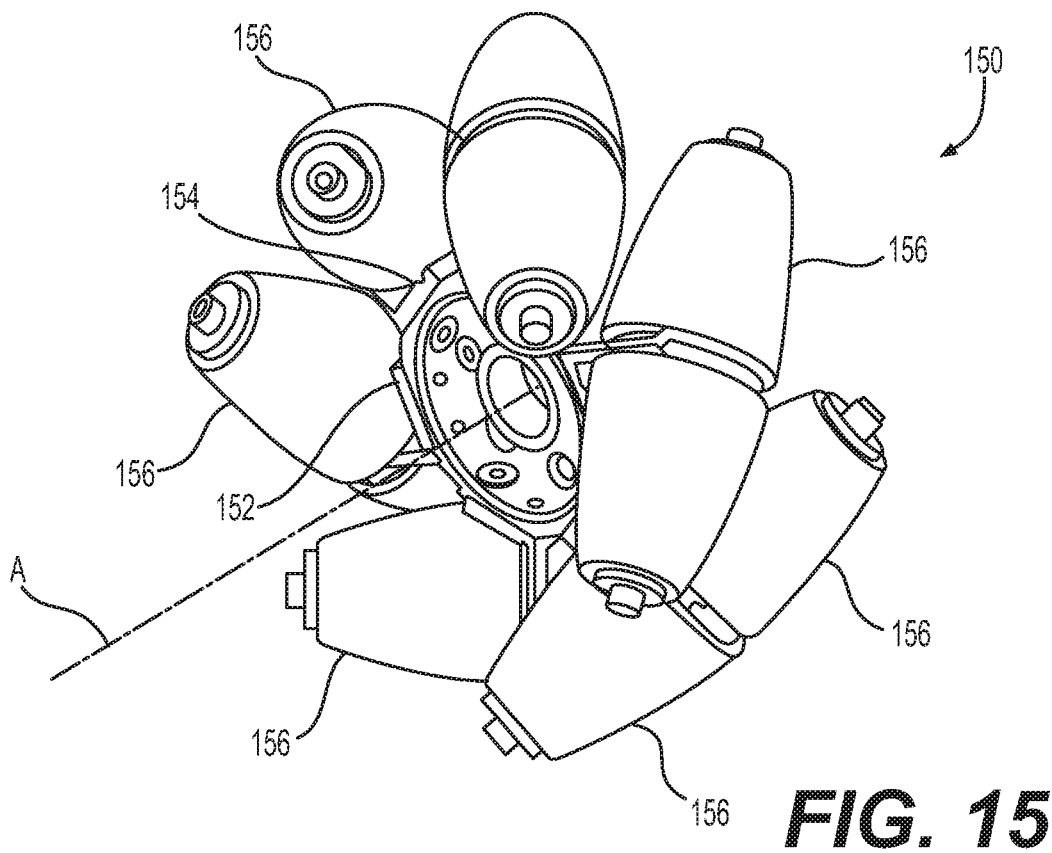
FIG. 15 is a perspective view of an example of a third omni-wheel useful in the present disclosure.

FIG. 15 depicts another type of omni-directional wheel 62, 64, a Mecanum wheel 150, useful in the present disclosure. Wheel 150 includes a central hub 152 with a central hub axis A and a plurality of flat circumferential surfaces (not shown). Each surface mounts a protruding spoke 154, which is then used to mount a circumferential roller 156. In this wheel 150, only one or two of the rollers 156 is on the floor or surface at a time, making turning easier. These types of wheels 150 are described in U.S. Pat. No. 8,011,735, which is hereby incorporated by reference in its entirety.

Figure 16:
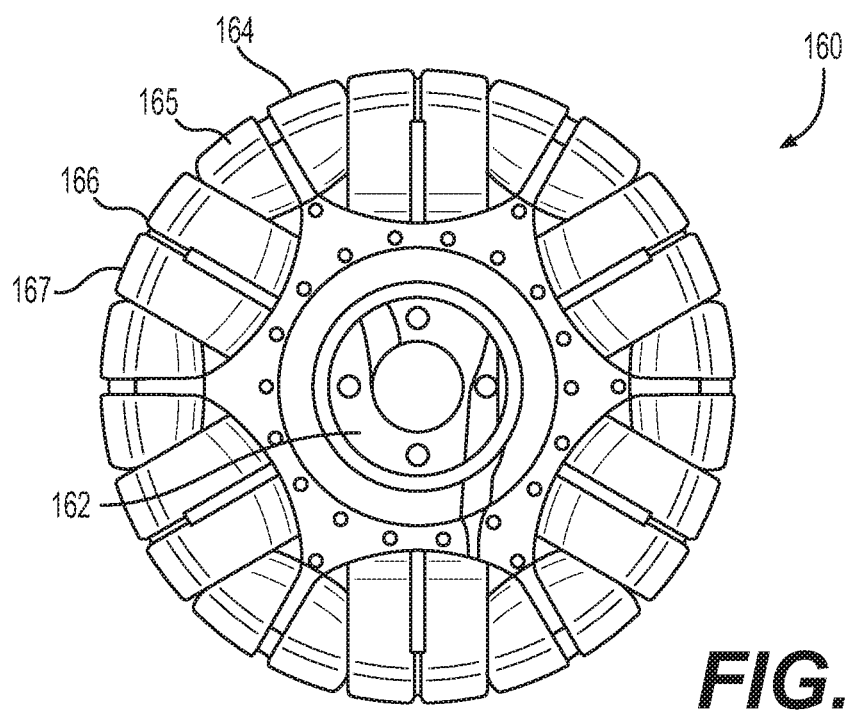
FIG. 16 is an elevational view of an example of a fourth omni-wheel useful in the present disclosure.

Yet another type of omni-directional wheel 62, 64, wheel 160 is disclosed in FIG. 16. Wheel 160 includes a central hub 162 which mounts two series of spokes or mounts 164, 166. Each of the first series of spokes 164 mounts a wheel 165 whose axis of rotation is ninety-degrees opposed to a direction of rotation of wheel 160 and central hub 162. Each of the second series of spokes 166 mounts a wheel 167 whose axis of rotation is also ninety-degrees opposed to a direction of rotation of wheel 160. Second series 166 of wheels have a slightly larger diameter than the first series 164 of wheels. Wheel 160 can rotate about an axis (not shown) perpendicular to its central hub 162. Rollers 165, 167 allow the wheels to easily change direction, thus making this a suitable omni-wheel 62, 64. These types of wheels 160 are described in U.S. Pat. Appl. 2015/0130260, which is hereby incorporated by reference in its entirety. Other types of Mecanum or omni-directional wheels 62, 64 may also be used in embodiments of this disclosure.

Once the location of the portable imaging system 10 is set in the operating room, the portable imaging system 10 may be locked into position. For example, the omni-directional wheels 62, 64 may be locked such that they are unable to move. In the alternative, a kickstand or other locking mechanism may be employed to prevent movement of the portable imaging system 10. Once the locking mechanism is released, the portable imaging system 10 is again free to move in any direction as described herein.

The advantages of this disclosure include the ability to accurately position large equipment in any desired position or direction, using the three-axis, three-degrees of freedom capabilities described above. The on-board GPS system may also be used to track the position of the equipment and to store and recall positions where the equipment is used. The unique three-axis motion capability of the omni-wheels 62, 64 includes a vertical rotary axis, which may be chosen as desired. By using both motion control and imaging control, the operator or diagnostic person can coordinate the position of the system with the desired position of the imaging equipment. The gantry position, as noted above, may be made via a robotic arm control or manual control. The precise positioning made possible by the motion control system, the encoders and the omni-wheels 62, 64 allows the portable imaging system 10 to have the control and precision of a fixed, non-mobile system.

The motion control system, the sensors, the encoders and the system memory allow the portable medical imaging system to act as a smart system. The sensors allow one to position the system as desired using the sensors and the memory. The system includes capabilities for precise, small movements for a particular image of a patient, as well as a transport mode, e.g., for moving to another patient or to another room. This allows users to park the system in a more convenient location and then to recall the imaging system to a precise location when desired. The system's memory gives users the ability to quickly and accurately recall the imaging cart to a particular position when it is needed later. The system may also use a series of fine movements to take a series of images for later combining, e.g., to stitch images together for a larger field-of-view. When a robot or robotic arm is used to position the imaging devices on the movable station, the ability of the station to quickly and accurately restore its position adds to the capability of the robot or robotic arm and can be considered to add a range of motion to such medical robots.

The foregoing makes it clear how the degrees of freedom of the portable medical imaging system 10 are helpful in positioning the system and in capturing images. The ability to simultaneously move both the signal transmitter and the sensor, for example by rotating them in an arc, allows rapid scans, that is, computerized tomography. The ability to simultaneously translate the signal transmitter and sensor, that is, in the x-y plane as described above, allows the system to also capture images of larger objects or an increased field-of-view. As shown in FIG. 17A, for example, the imaging system 170 may include an inner arm 171 mounting a signal transmitter 174 and a detector or sensor 176, for example, directly opposite from one another. As described above, the transmitter 174 and sensor 176 are mounted so that they are at opposed ends of a 180-degree arc. Thus, upon 360-degree rotation of the gantry, for example, described with reference to FIGS. 9A-9G, the area of 172 is completely imaged by the imaging device.

The radius of the inner arm 171 allows scanning of object 172, a portion thereof, or a focal point within the boundary defined by object 172. The midpoint of object 172 is centrally located between the transmitter 174 and the sensor 176. As shown in FIG. 17A, the divergence or width of the signal or x-ray beam 175 from its source 174 is sufficient to capture all aspects of the target or object 172 or a portion of an object contained within the radius defined by 172. Thus, in FIG. 17A, the field-of-view (FOV) of the signal or x-rays transmitted from transmitter 174 is able to capture all portions of target or object 172 or a portion of an object contained within the radius defined by 172. It will be appreciated that the object, in some instances, may indeed be larger than the area identified as object 172. The sensor 176, as shown here, is also sufficiently large to capture x-ray or other signals received from the transmitter 174 and transmitted through the object 172 or a portion thereof whose image is desired.

On occasion, there may be a need to image a target or object that is larger than the field-of-view depicted in FIG. 17A. Thus, as shown in FIG. 17B, object 178 is larger than the width 175 of the signal. However, by moving the location of the transmitter 174 and sensor 176 off-center, upon the 360-degree rotation of the gantry (see e.g., FIGS. 9A-9G illustrating the movement in 60 degree increments), a larger field-of-view encompassing the entire object 178 is obtained. As shown in FIG. 17B, the signal transmitter 174 and detector or sensor 176 are both moved off-center a specific distance 177. In this example, the distance moved, or offset, is sufficient so that the field-of-view of the transmitter 174 now captures the entirety of the target or object 178 as the inner arm 72 of the gantry is rotated. Again, it will be appreciated that the object may actually be larger than the portion identified as 178. In this example, the portable medical imaging cart did not move, e.g., translate, rather the signal transmitter 174 and the detector or sensor 176 are in a fixed position at distance 177 from the center line or are translated to off-center the required distance 177. By offsetting the distance 177 of the transmitter 174 and sensor 176, it was discovered that the larger field-of-view could be obtained without the need for rotation about a focal spot at the center of the object to be imaged and without the need for a traditional O-shaped gantry. It will be appreciated that the location of the transmitter 174 and sensor 176 may be fixed in this position or may be movable, for example, along a translation device as described in more detail below.

FIGS. 17A-17B thus depict an additional degree of freedom, the ability of the signal transmitter 174 and the detector or sensor 176 to translate, for example, in a linear fashion. FIGS. 18A-18B depict examples of at least one way this can be accomplished. In FIG. 18A, the signal transmitter 174 is mounted on a track, linear actuator, or other translational device 184. For example, the translational device 184 may be mounted in a linear track 182. In a similar manner, on the other side of arm 171, located 180-degrees opposite, the sensor or detector 176 is also mounted on a track, linear actuator, or other translational device 188, for example, in a track 186. As depicted by the arrows and phantom-line representations, the signal transmitter 174 and the detector or sensor 176 are capable of moving in a single axis, left and right. Thus, the transmitter 174 and sensor 176 are able to be positioned off-center in order to increase or narrow the field-of-view of the imaging space.

The linear axis provided by the translational devices 184, 188 may be oriented as desired by the user, thus providing for more precise control in virtually any desired orientation. Just as a rotary axis can be more precise than using two linear axes, this new axis may be placed as desired by orienting the gantry 56, the outer arm 70, the inner arm 72, gantry vertical shaft 59 z-axis, and even the movable station 60, in a desired orientation. Thus, as shown in FIG. 17B and in FIGS. 18A-18B, and with reference to FIG. 1 the axis is placed along the x-axis, with translation forward and backward or along the y-axis with translation left and right. With respect to FIG. 3, with transmitter 74 and sensor 76 will move up and down, along the z-axis. With respect to FIG. 4, with the gantry 56 now oriented horizontally, the new axis will also translate parallel to the x-axis as shown. In addition, the gantry and outer arm 72 are positioned in a variety of non-horizontal and non-vertical orientations in FIGS. 9B, 9C, 9E and 9F. Translational devices 184, 188 thus form an independent degree of freedom along what may be termed an intermediate or otherwise desired orientation. The transmitter 174 and sensor 176 may thus be advantageously oriented to image a particular injury, tumor, or other medical phenomenon with a larger field-of-view than traditional imaging devices.

The transmitter 174 and sensor 176 may be moved or adjusted as desired to use the larger field-of-view that is now possible. For example, the transmitter 174 and sensor 176 may be rotated in sequence to several positions to ensure complete coverage of the desired area or volume of the target. The "targeting" may be done before imaging. The desired positions may be noted and recorded in the memory 44 or in other memory available in the imaging control module 54. When the images are taken, the imaging operator or health-care professional need only sequence through the desired series of images. This can ensure complete and accurate coverage, the rotations or movements accomplished after each image is taken, so that the images are not blurred.

Translational devices or linear actuators may include motorized electric linear actuators, linear tracks, linear slides, ball slides, rack slides, ball screws, and the like to provide movement along a straight line. Translational devices 184, 188 may be controlled by the motion control module 51, thus ensuring coordinated movement of all components of the portable medical imaging device. In particular, the movements of translational devices 184, 188 may be controlled so that they are identical. Thus, when either device moves to the left or to the right, the other may also move in a coordinated manner, thus ensuring coverage of the object 178 to be imaged and also ensuring that signals sent from transmitter 174 will be captured by sensor 176 after traversal through the patient or other object to be imaged. This also prevents any escape of harmful radiation and limits exposure of the patient and diagnostic and health-care workers. The movements of the signal transmitter 174 and detector or sensor 176 are coordinated and controlled, as are the other movements of devices under the control of the motion control module. In this embodiment, each linear actuator, ballscrew or motor may include its own encoder for positional feedback, as described above for other motors or actuators of the portable medical imaging system 10.

In an alternative embodiment, the transmitter 174 and/or sensor 176 may be fixed in position. For example, transmitter 174 and sensor 176 may be fixed in position at distance 177 from center such that the equipment always images with the enlarged field-of-view. In another embodiment, if the area of the sensor 176 is large relative to the transmitter 174, then the sensor 176 may be stationary even if the transmitter 174 moves or translates so long as the sensor 176 is still able to detect the transmissions of the transmitter 174.

The translational movement, depicted in FIGS. 17A-17B and 18A-18B, may ensure coverage of the object to be imaged. Without such coordination and enhanced field-of-view capabilities, a much larger imaging device would be required. That is, the C-arms 70 and 72 would need to have a much larger diameter for complete coverage of the object 178 to be accomplished. Without the separate movements of outer C-arm 70 and inner C-arm 72, the portable imaging device might actually need a complete circle, an O-shaped gantry or gantry mount, to achieve complete 360-degree coverage. For example, some prior art devices, such as those in U.S. Pat. No. 7,108,421 achieve coverage of larger objects by rotating a larger translating apparatus to different positions about the object. The larger motion can require an O-shaped gantry or gantry mount, for example, at greater expense, with greater limitations for freedom of movement, and limitations in the operating room environment.

In contrast, embodiments of the present disclosure are able to cover larger objects and have a much larger field-of-view to be imaged by using small movements of the portable medical imaging system and its components. Examples of movements will be made with reference to FIGS. 1, 3 and 4. In FIG. 1, for example, gantry 56 is in a generally vertical orientation, with C-arms 70, 72 positioned about patient bed 26, ready for a patient. Imaging transmitter 74, below the patient, will work in coordination with detector 76, above the patient. The example discussed with reference to FIGS. 18A-18B requires movement in the left-right or horizontal direction, i.e., in the plane of the arm 171. With reference to FIG. 1, it can be seen that this is movement in the y-axis direction.

Figure 4:
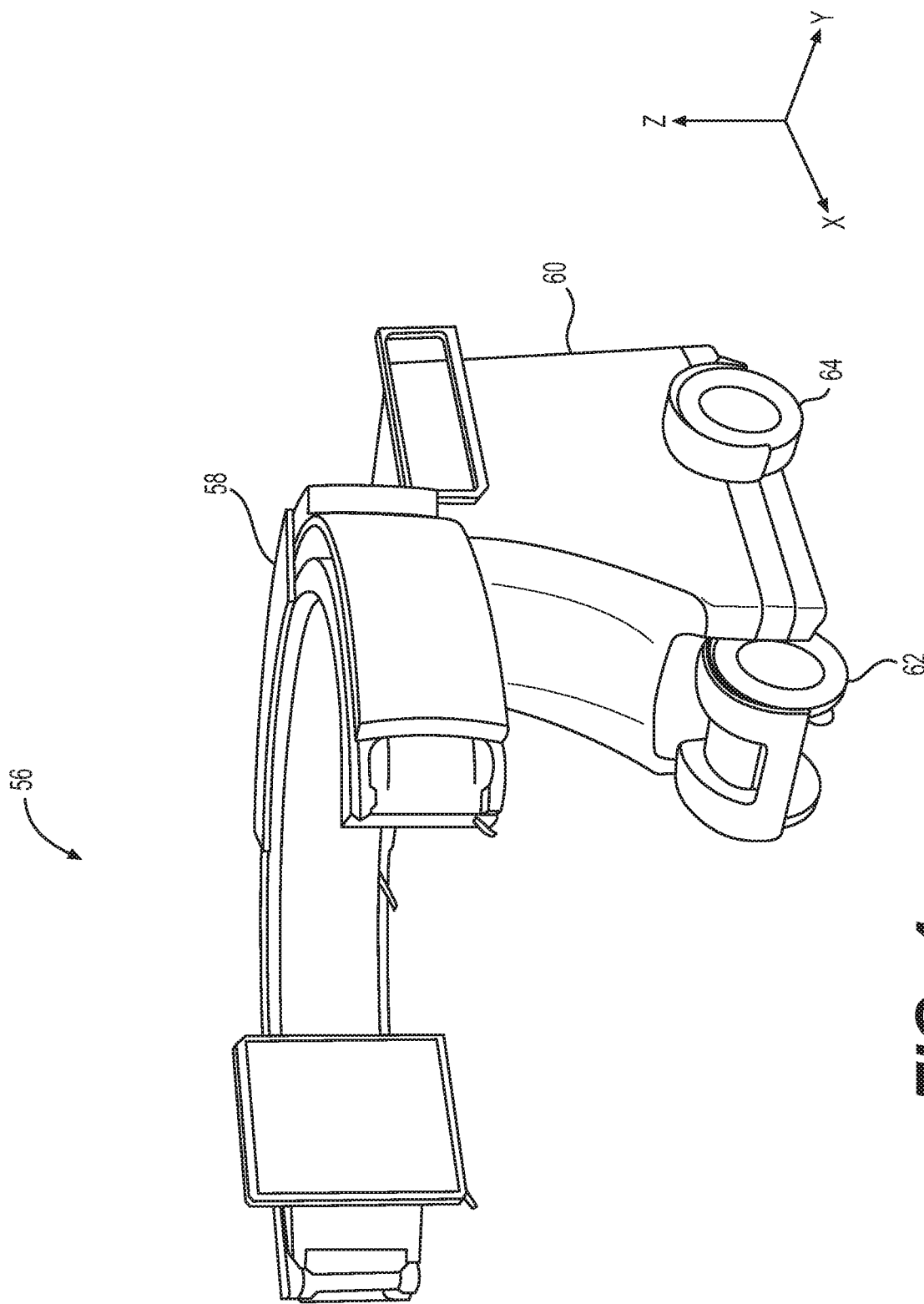
FIG. 4 is a perspective view of the imaging system of FIG. 1 in which the gantry has been rotated about the X-axis by 90 degrees.

In FIG. 3, the gantry 56 is in the same vertical orientation, but the inner arm 72 has rotated ninety-degrees, so that the transmitter 74 and sensor 76 are now oriented horizontally. This is the "rotor" rotational degree of freedom, parallel to the y-axis, previously discussed. Translating the transmitter 74 and sensor 76 in the plane of arm 72 now would be vertical movement, i.e., along the z-axis as shown in FIG. 3. With reference to FIG. 4, the gantry 56 has now rotated ninety-degrees to a horizontal position. If inner arm 72 were equipped with the linear translational devices of FIGS. 18A-18B, transmitter 74 and sensor 76 would translate within the plane of inner arm 72 in the x-axis direction depicted in FIG. 4. Rotation about the x-axis, or parallel with the x-axis, is the "tilt" degree of freedom discussed above. Thus, while the transmitter 74 and sensor 76 themselves have only a single degree of freedom, along one linear axis, that axis may be used in the context of the portable medical imaging system. Thus, the linear movement may be across a width of a patient, per FIGS. 1 and 4, or vertically up and down with respect to a patient, per FIG. 3.

With reference to these same figures, the other degrees of freedom as previously discussed, may also be considered. Thus, in FIG. 1, the outer 70 and inner 72 arms allow rotational degrees of freedom about the patient bed 26. Vertical shaft 59 allows vertical translation, i.e., linear movement along the z-axis. The omni-wheels 62, 64 allow complete freedom of movement within the x-y plane. These degrees of freedom may also be used when the medical team wishes to capture images of the patient to be mounted on patient bed 26. The portable medical imaging system 10 thus allows the six-degrees of freedom previously discussed, and also has a new linear-axis degree of freedom, as shown in FIGS. 17A-17B.

These degrees of freedom allow for additional uses of the portable medical imaging system. For example, smaller and more precisely controlled movements along the axes may now be used, rather than larger movement. For example, and as shown in FIGS. 17A-17B, if the object to be imaged is larger than can be conveniently handled, the linear degree of freedom arising from the translational movement, thereby enables an enlarged field-of-view.

Figure 19:
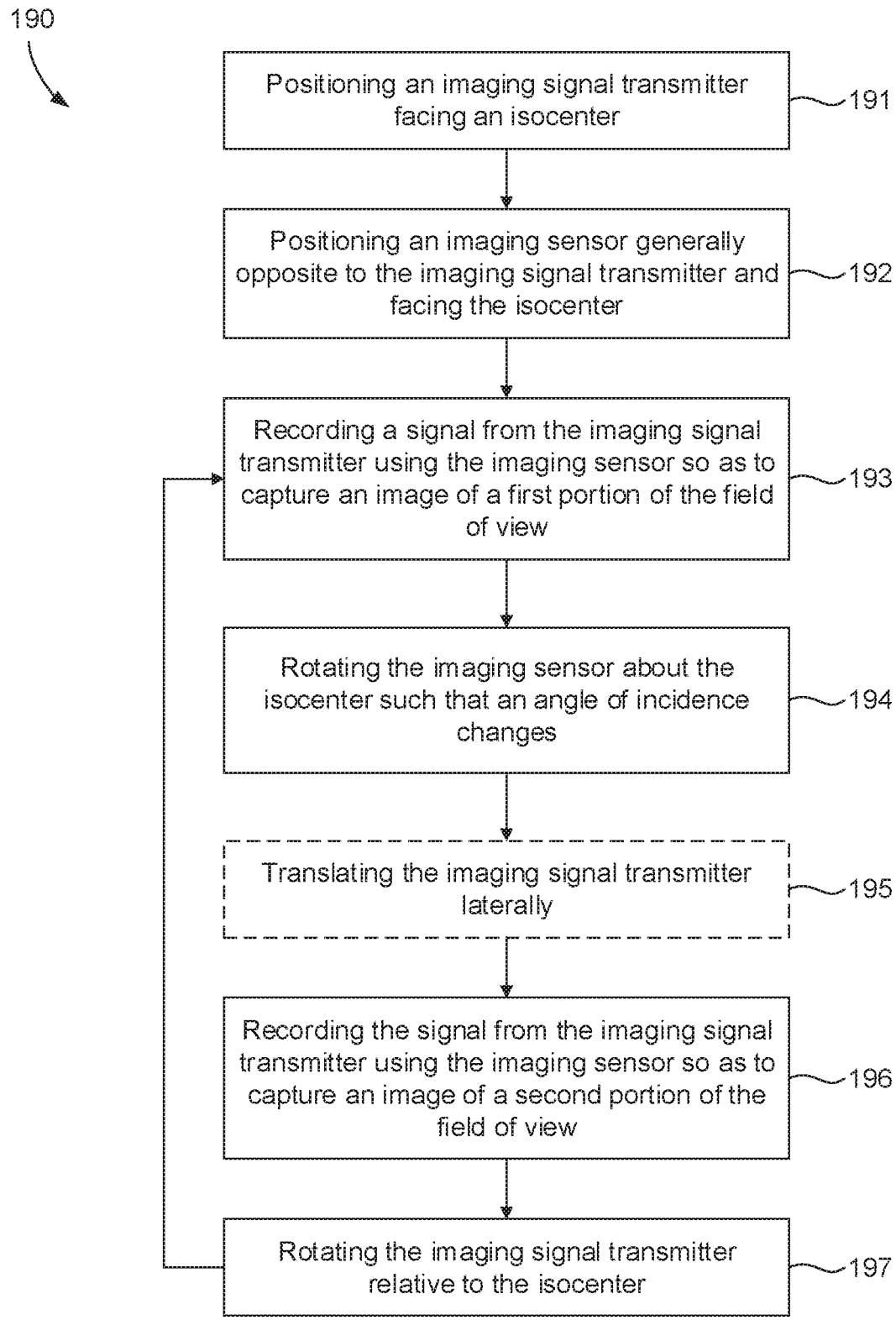
FIG. 19 is a flowchart of a method for imaging using an imaging system, particularly for enlarging the field-of-view (FOV), according to an embodiment of the present disclosure.

FIG. 19 illustrates a flowchart of an embodiment of a method 190 for imaging an object using a portable medical imaging system, such as one or more embodiments of the system disclosed above. In particular, the method 190 may be employed to enlarge the field-of-view (FOV) of the system 10, without enlarging a zone of collision thereof, as will be described in greater detail below.

Figure 20:
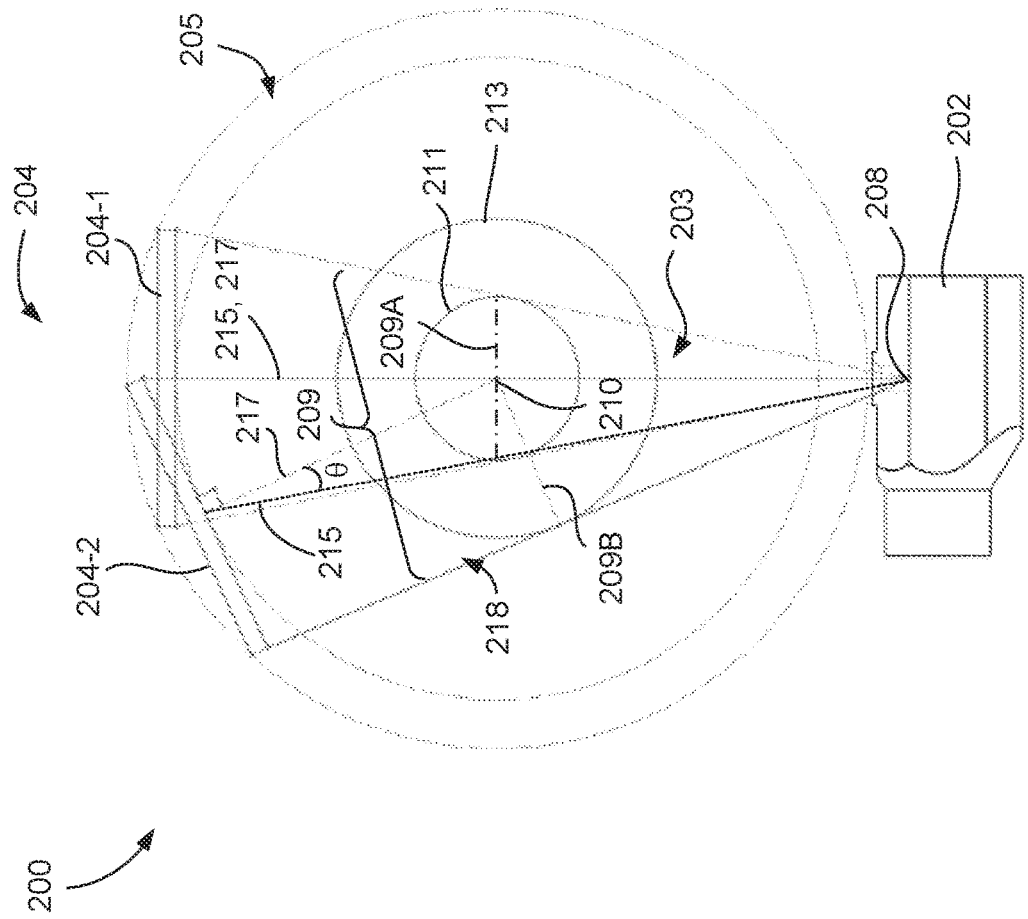
FIG. 20 depicts a diagram of the imaging sensor being rotated about the center axis of the gantry to enlarge the FOV, according to an embodiment of the present disclosure.

Referring now to FIG. 20, there is shown a diagrammatic example of an imaging system 200 executing an embodiment of the method 190. The method 190 will be described herein with reference to the imaging system 200 by way of example. The imaging system 200 includes an imaging signal transmitter 202 and an imaging sensor 204, which are coupled to a gantry, C-arm(s), etc., as discussed above. The imaging signal transmitter 202 and the imaging sensor 204 may be coupled to the gantry via separate actuators (translation devices), or otherwise provided with functionality enabling the imaging signal transmitter 202 and the imaging sensor 204 to move independently of one another.

The imaging system 200 also defines a zone of collision 205, which is a generally annular area defined by the extent of possible positions for the imaging sensor 204. The imaging sensor 204 may be exposed in some embodiments of the system 200, and may represent the inner-most extent of the movable components attached to the gantry. Care is thus taken to ensure nothing obstructs the zone of collision 205, which would otherwise impede the operation of the system 200 by blocking movement of the imaging sensor 200. If the imaging sensor 204 is allowed to translate (as discussed above with respect to FIGS. 17A and 17B) or rotate about a point other than the center axis, the zone of collision 205 may expand (i.e., the outer circle defining the annular zone of collision 205 in FIG. 20 may increase in size or diameter). In some cases, it may be advantageous to minimize the zone of collision 205, e.g., to what it would be if the imaging sensor 204 were not movable by translation or rotation about a point other than the central axis, while increasing the FOV.

As shown, the imaging signal transmitter 202 may transmit a signal 203 (e.g., X-ray), which may be received by the imaging sensor 204. The signal 203 may define a focal point 208, which may be located at the image signal transmitter 202. The signal 203 may also define a first portion 209A of a field-of-view (FOV) 209, which may produce an image of an object 211 positioned therein. In some situations, it may be desirable to increase the size of the FOV 209 beyond what the image sensor 204 is sized to provide with a single image, e.g., by adding a second portion 209B to the FOV 209, as will be described below. Such additions to FOV 209 may allow an object 213 larger than the object 211 and/or larger than the first portion of the FOV 209A to be imaged.

Further, the imaging sensor 204 may be rotatable about a point that is between the image signal transmitter 202 and the image sensor 204, e.g., an isocenter 210 located at or near a central axis of the gantry. The point, e.g., the isocenter 210, may be configured to correspond to a generally central location of an object to be imaged, and may be generally equidistant from the image sensor 204 and the image signal transmitter 202. By constraining rotation to being about the isocenter 210, the zone of collision 205 is not expanded or remains approximately the same. In other embodiments, the point may be another point (or points) between the image signal transmitter 202 and the image sensor 204.

In addition, an angle of incidence θ of the signal 203 may be defined by a line 215 drawn from the focal point 208 to the middle of the imaging sensor 204, and a line 217 normal to the imaging sensor 204. This may be a measurement or representation of how far from parallel the image signal transmitter 202 and the image sensor 204 are oriented with respect to each other. Rotation of the sensor 204 or transmitter 202 relative to the other thus changes the angle of incidence θ. Accordingly, for example, rotating the imaging sensor 204 about the isocenter 210 between the two positions 204-1, 204-2, while holding the imaging signal transmitter 202 stationary, results in changing the angle of incidence θ. Thus, in FIG. 20, the lines 215, 217 are collinear for position 204-1 (angle of incidence θ is zero), and are separated by some non-zero angle at position 204-2.

Turning again to the method 190 shown in FIG. 19, and still referring to the system 200 of FIG. 20, the method 190 may include positioning the imaging signal transmitter 202 such that it is facing a specific point (e.g., isocenter 210), as at 191. It will be appreciated that "facing" does not necessarily mean that the sensor is normal to a ray extending radially outward from the focal spot of the imaging signal transmitter 208, but allows for some deviation from normal, for example, from about 0.01 degree to about 20 degrees from normal in some embodiments. In some embodiments, nonetheless, the imaging sensor 204 may be normal to such a ray.

The method 190 may also include positioning the imaging sensor 204 generally opposite to the imaging signal transmitter 202 such that the imaging sensor is facing the isocenter 210, as at 192. It will be appreciated that "generally opposite" does not necessarily mean 180 degrees apart about the center axis, but allows for some range of angles across which the transmitter 202 may transmit signals toward the sensor, which are then captured by the sensor 204 to form an image of at least part of an object therebetween. For example, in some embodiments, the imaging sensor 204 may be about 180 degrees+/−5 degrees opposite from the imaging signal transmitter 202. At this point, the angle of incidence θ may, in one example, be 0 degrees, as shown for position 204-1, but this is merely an example, and in other starting positions, the angle of incidence θ may be non-zero such as 30 degrees.

The method 190 may further include recording the signal 203 from the imaging signal transmitter 202 using the imaging sensor 204, so as to capture an image of the first portion 209A of the FOV 209, as at 193. The first portion 209A may encompass the isocenter 210, as shown. Further, the size of the first portion 209A may be dictated by the distance between the imaging signal transmitter 202 and the imaging sensor 204, and the geometry of the components thereof.

The method 190 may further include rotating the imaging sensor 204 about the isocenter 210 such that the angle of incidence θ changes, as at 194. This is illustrated in FIG. 20 as moving between the first and second positions 204-1, 204-2. In addition to rotating about the isocenter 210, this movement of the imaging sensor 204 also results in rotation about the focal point 208, as the imaging signal transmitter 202 does not, at 194, rotate around the isocenter 210, along with the imaging sensor 204. This, in turn, causes the angle of incidence θ to change, in this case, from zero to some non-zero number, as mentioned above.

The method 190 then includes recording another signal 218 from the imaging signal transmitter 202 using the imaging sensor 204 so as to capture an image of the second portion 209B of the FOV 209, as at 196. As the imaging sensor 204 is rotated, the location or path of the signal 218 where it passes through the object 213 changes from the location or path of the signal 203. Accordingly, the second portion 209B of the FOV 209 is defined by the location or path of the second signal 218 and the second portion 209B may be added to the first portion 209A. The first and second portions 209A, 209B may be overlapping or abutting, and thus adding them together increases the overall FOV 209. Further, in some embodiments, the isocenter 210 is maintained within both portions 209A, 209B. It will be readily appreciated that multiple rotational positions for the imaging sensor 204 with respect to the isocenter 210 may be employed without corresponding rotation of the imaging signal transmitter 202, thereby increasing the FOV in both lateral directions.

In the second position 204-2, since the angle of incidence θ has changed (in this example, from zero to non-zero), imaging correction may be employed, which correction may be based on or calculated using the angle of incidence θ. In order to reconstruct the image volumes using projected images taken with an offset and tilted panel (e.g., with the imaging sensor 204 in the second position 204-2), intensity correction and pixel size scaling are conducted. Further, the Feldkamp weights for each projection data are adjusted based on the offset from the center of the panel. Where there is redundant data on the panel (the overlap between the first and second portions 209A, 209B), the data in this region receives greater weight for proper image reconstruction. An example of this weight function is referenced in Ge Wang, *X-ray micro-CT with a displaced detector array*, 29 Med. Phys. 9 (2002), which is incorporated herein by reference to the extent not inconsistent with the present disclosure.

Figure 21:
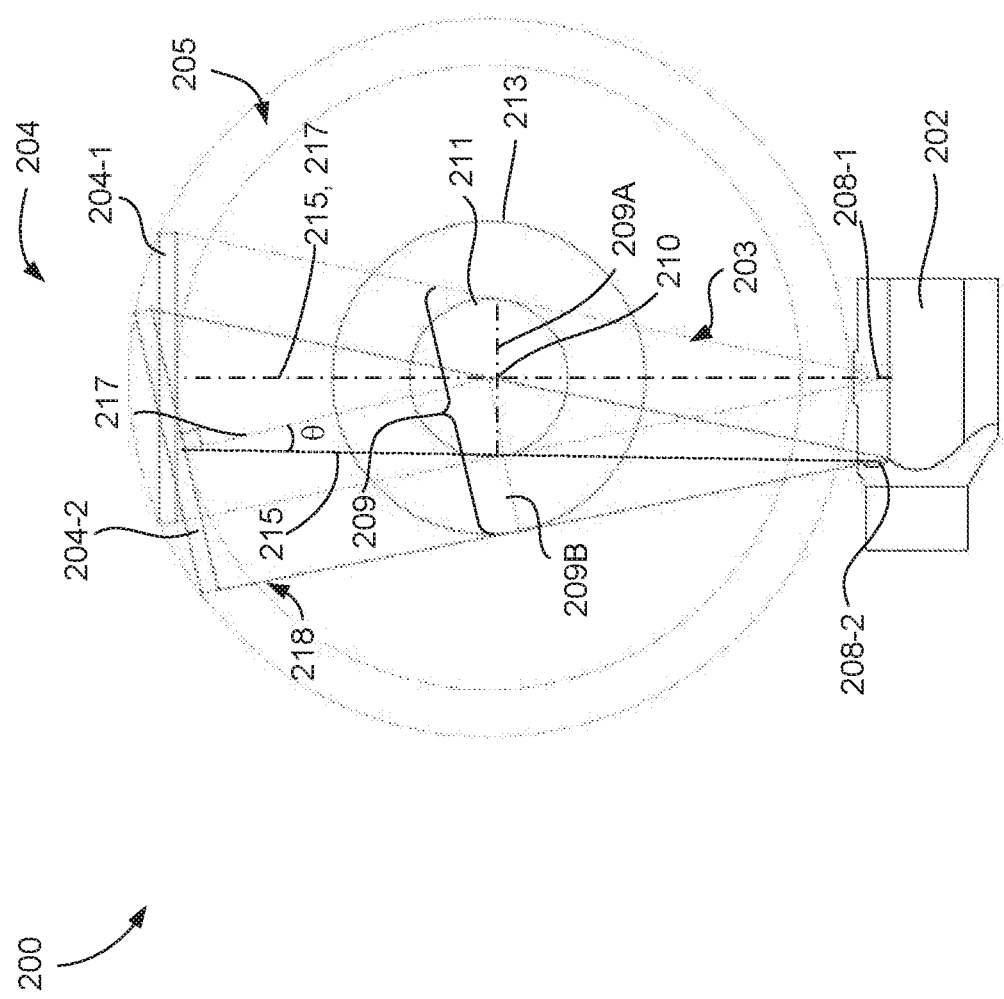
FIG. 21 depicts a diagram of the imaging sensor being rotated about the center axis of the gantry, while translating the imaging signal transmitter, to further enlarge the FOV, according to an embodiment of the disclosure.

Still referring to FIG. 19, but now additional referring to FIG. 21, there is shown another diagrammatic example of an execution of the method 190 using the system 200. In this embodiment, the method 190 additionally includes translating the imaging signal transmitter 202 perpendicular to the center axis (e.g., laterally moving the imaging signal transmitter 202), as represented in 2-D by the isocenter 210, as at 195, in addition to rotating the imaging sensor 204 respect to the isocenter 210 (as at 194). As such, the focal point 208 moves from a first position 208-1 to a second position 208-2, and the angle of incidence θ also changes. The second image is then captured (as at 196), with the resulting FOV 209 being further expanded, and again without expanding the zone of collision 205 or wherein the zone of collision 205 remains approximately the same.

Once scans across two or more such rotational positions 204-1, 204-2 of the imaging sensor 204 with respect to the isocenter 210 are complete (and/or two or more positions of the imaging signal transmitter 202), and a desired FOV 209 is imaged, the method 190 may proceed to rotating at least the imaging signal transmitter 202 with respect to (e.g., around) the isocenter 210, so as to achieve a different perspective from which to image the field-of-view, as at 197. In some embodiments, the imaging sensor 204 may also be moved at this time, (e.g., before executing 193), such that the FOV 209 continually includes the isocenter 210. Upon reaching a new position (e.g., similar to position 204-1, but with both the imaging sensor 204 and the imaging signal transmitter 202 rotated about the isocenter 210), the above-described process of rotating the imaging sensor 204 with respect to the isocenter 210 while maintaining a rotational position of the imaging signal transmitter 202 (and, in some embodiments, translating the imaging signal transmitter 202) may be repeated (e.g., as at 194, 195, and/or 196). This, in turn, may be repeated until a 360-degree view of the field-of-view is captured (e.g., a series of images taken from all around the FOV 209).

One of ordinary skill will recognize that the example of a method 190 shown in FIG. 19 is presented for conciseness and clarity of explanation and that operations, functions, stages, and/or step may be added to, deleted from, reordered, performed simultaneously or modified in the method 190 without departing from the principles of the invention. For example, as noted, the operation denoted by 195 may be omitted or performed optionally. Other variations are possible.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference, as if each such patent or publication were individually incorporated by reference herein. Various features and advantages of the invention are set forth in the following claims.

What is claimed is:

1. A method for imaging using a portable medical imaging system comprising a double telescoping C-gantry, an imaging signal transmitter and an imaging sensor, the method comprising:

positioning the imaging signal transmitter and the imaging sensor opposite to one another, wherein the imaging sensor defines an angle of incidence with respect to a signal emitted from the imaging signal transmitter, wherein the imaging sensor and imaging signal transmitter, in an initial position, define a central axis from the imaging sensor to imaging signal transmitter, the central axis being between the imaging sensor and the imaging signal transmitter and being the central axis of the gantry, and a first isocenter located at the central axis, the first isocenter being equidistant between the imaging signal transmitter and the imaging sensor, wherein the angle of incidence is defined as a first line from a focal point of the imaging signal transmitter to a middle of the imaging sensor and a second line normal from the imaging sensor to the first isocenter, wherein the angle of incidence is zero at the initial position, and the imaging signal transmitter and the imaging sensor being attached to the double telescoping C-gantry;

controlling the movement of the telescoping C-gantry to minimize a zone of collision, the zone of collision being an annular area defined by an extent of possible positions for the imaging sensor, recording a first signal from the positioned imaging signal transmitter using the positioned imaging sensor, so as to capture an image of a first portion of a field-of-view;

rotating the imaging sensor such that the angle of incidence changes while the second line remains normal from the imaging sensor to the first isocenter; and recording a second signal from the imaging signal transmitter using the rotated imaging sensor, so as to capture an image of a second portion of the field-of-view.

2. The method of claim 1, wherein the double telescoping C-gantry is configured to provide a 360 degree imaging beam rotation.

3. The method of claim 1, further comprising combining the first and second portions of the field-of-view.

4. The method of claim 1, wherein the isocenter is within the first and second portions of the field-of-view.

5. The method of claim 1, further comprising maintaining a rotational position of the imaging signal transmitter while rotating the imaging sensor, such that the rotational position of the imaging signal transmitter is the same when transmitting the first and second signals.

6. The method of claim 1, further comprising translating the imaging signal transmitter linearly after recording the first signal and before recording the second signal.

7. The method of claim 1, further comprising:

after recording the second signal, rotating the imaging signal transmitter and the imaging sensor about the isocenter; after rotating the imaging signal transmitter and the imaging sensor about the isocenter, recording a third signal from the imaging signal transmitter using the imaging sensor, so as to capture an image a first portion of a second field-of-view; rotating the imaging sensor about the isocenter such that the angle of incidence changes from when the third signal was recorded; and recording a fourth signal from the imaging signal transmitter using the imaging sensor, so as to capture an image of a second portion of the second field-of-view.

8. A portable medical imaging system comprising:
a movable station comprising a double telescoping C-gantry, the C-gantry including movable first and second C-arms;
an imaging signal transmitter attached to the movable first C-arm; and
an imaging sensor positioned opposite to the imaging signal transmitter and attached to the movable first C-arm, wherein the imaging sensor defines an angle of incidence with respect to a signal emitted from the imaging signal transmitter,
wherein, at an initial position the imaging sensor and the imaging signal transmitter define a central axis, the central axis being between the imaging sensor and the imaging signal transmitter and being the central axis of the gantry, and an isocenter located at the central axis and being equidistant between the imaging signal transmitter and the imaging sensor,
wherein the angle of incidence is defined as a first line from a focal point of the imaging signal transmitter to a middle of the imaging sensor and a second line normal from the imaging sensor to the isocenter,
wherein the angle of incidence is zero at the initial position, wherein the imaging sensor is configured to rotate about the isocenter and relative to a point approximately on a central axis of the movable first C-arm independently of the imaging signal transmitter, so as to change an angle of incidence for a signal transmitted from the imaging signal transmitter to the imaging sensor while the second line remains normal from the imaging sensor to the isocenter, and provide a field-of-view that is larger than the field-of-view of the imaging sensor at a single position,
wherein the C-gantry is moved to minimize a zone of collision, the zone of collision being an annular area defined by an extent of possible positions for the imaging sensor.

9. The portable medical imaging system of claim 8, wherein the imaging sensor is configured to face the isocenter on the central axis while being rotated.

10. The portable medical imaging system of claim 8, wherein the imaging sensor is configured to capture a first image before rotating independently of the imaging signal transmitter and to capture a second image after rotating independently of the imaging signal transmitter, and wherein the portable medical imaging system comprises a controller that is configured to combine the first and second images to produce the enlarged field-of-view.

11. The portable medical imaging system of claim 8, wherein the imaging signal transmitter and the imaging sensor are configured to rotate about the isocenter so as to provide a 360 degree view of an object between the imaging signal transmitter and the imaging sensor.

12. The portable medical imaging system of claim 8, further comprising a translational device mounting the imaging signal transmitter to the movable first C-arm, wherein the translation device is configured to translate the imaging signal transmitter laterally with respect to the central axis.

13. The portable medical imaging system of claim 8, further comprising:
a gantry mount attached to the movable station and to the C-gantry; and
wherein the first C-arm and the movable second C-arm together provide a 360-degree rotation of the imaging signal transmitter and the imaging sensor.

14. The portable medical imaging system of claim 12, wherein the translational device is adapted for movement along a linear axis in an orientation that is perpendicular or parallel to an axis of a Cartesian coordinate system.

15. The portable medical imaging system of claim 14, wherein the linear axis provides a linear degree of freedom in capturing an image of an object.

16. A portable medical imaging system, comprising:
a movable station;
a gantry mount attached to the movable station;
a gantry rotatably attached to the gantry mount and including a first C-arm slidably mounted to and operable to slide relative to the gantry mount;
a second C-arm including a imaging signal transmitter and an imaging sensor and slidably coupled to the first C-arm, the first and second C-arms together providing a 360-degree rotation about an object to be imaged; and
a control system for controlling motion of the movable station and first and second C-arms, and for controlling imaging of the portable imaging system, wherein the control system is configured to cause the portable medical imaging system to perform operations,
wherein the imaging sensor defines an angle of incidence with respect to a signal emitted from the imaging signal transmitter, wherein the imaging sensor and the imaging signal transmitter, in an initial position, define a central axis from the imaging sensor to imaging signal transmitter, and the central axis being between the imaging sensor and the imaging signal transmitter and being the central axis of the gantry, and an isocenter located at the central axis, the first isocenter being equidistant between the imaging signal transmitter and the imaging sensor,
the angle of incidence is defined as a first line from a focal point of the imaging signal transmitter to a middle of the imaging sensor and a second line normal from the imaging sensor to the first isocenter,
wherein the angle of incidence is zero at the initial position, wherein the imaging sensor is configured to rotate about the isocenter and relative to a point approximately on a central axis of the movable first C-arm independently of the imaging signal transmitter, so as to change an angle of incidence for a signal transmitted from the imaging signal transmitter to the imaging sensor while the second line remains normal from the imaging sensor to the isocenter.

17. The portable medical imaging system of claim 16, wherein the isocenter comprises an isocenter of the gantry.

* * * * *